(12) United States Patent
Kilbey

(10) Patent No.: US 9,498,374 B2
(45) Date of Patent: Nov. 22, 2016

(54) MODULAR SHOULDER CRYOTHERAPY SYSTEM AND METHOD

(71) Applicant: Bryan E. Kilbey, DeFuniak Sprs, FL (US)

(72) Inventor: Bryan E. Kilbey, DeFuniak Sprs, FL (US)

(*) Notice: Subject to any disclaimer, the term of this patent is extended or adjusted under 35 U.S.C. 154(b) by 876 days.

(21) Appl. No.: 13/874,618

(22) Filed: May 1, 2013

(65) Prior Publication Data

US 2014/0364925 A1 Dec. 11, 2014

(51) Int. Cl.
*A61F 7/10* (2006.01)
*A61F 7/00* (2006.01)
*A61F 7/02* (2006.01)

(52) U.S. Cl.
CPC ............ *A61F 7/10* (2013.01); *A61F 2007/003* (2013.01); *A61F 2007/0228* (2013.01); *A61F 2007/0231* (2013.01); *A61F 2007/108* (2013.01)

(58) Field of Classification Search
CPC combination set(s) only.
See application file for complete search history.

(56) References Cited

U.S. PATENT DOCUMENTS

| | | | | |
|---|---|---|---|---|
| 6,306,111 B1* | 10/2001 | Dean | ..................... | A61F 5/3753 128/DIG. 19 |
| 2001/0018604 A1* | 8/2001 | Elkins | ...................... | A61F 7/10 607/108 |
| 2007/0106356 A1* | 5/2007 | Carstens | .............. | A41D 13/005 607/112 |

* cited by examiner

*Primary Examiner* — Joseph Stoklosa
*Assistant Examiner* — Adam Avigan
(74) *Attorney, Agent, or Firm* — J. Wiley Horton

(57) ABSTRACT

A modular shoulder cooling system. A retention panel is affixed over the shoulder. The retention panel is held in position by a pair of straps attached to a belt around the user's waist. At least a portion of the inward facing surface of the retention panel is covered in loop material. Bags containing cooling medium are furnished. These are referred to as "cold packs." Each cold pack has a first side with a soft, tactilly pleasing surface. This first surface is intended to face the user. Each cold pack also has a second side intented to face the inward facing surface of the retention panel. This second side includes one or more hook panels configured to engage the loop material on the inward facing surface of the retention panel. The user can attach a cold pack or packs to the rentention panel by pressing the hook panels on each cold pack against the loop material on the retention panel. Thus, no pockets are required.

20 Claims, 23 Drawing Sheets

MODULAR SHOULDER CRYOTHERAPY SYSTEM AND METHOD

CROSS-REFERENCES TO RELATED APPLICATIONS

This application is a non-provisional application claiming priority to U.S. Provisional Application No. 61/640,902 filed on May 1, 2012.

STATEMENT REGARDING FEDERALLY SPONSORED RESEARCH OR DEVELOPMENT

Not Applicable.

MICROFICHE APPENDIX

Not Applicable

BACKGROUND OF THE INVENTION

1. Field of the Invention

This invention relates to the field of medical products. More specifically, the invention comprises a modular system for applying cryotherapy to a patient's shoulder.

2. Description of the Related Art

It is now widely recognized that the application and maintenance of "cold therapy" in the hours and days following surgery significantly improves patient outcomes. The terms "cold therapy" and "cryo therapy" are often used interchangeably. The present application will use the term "cryo therapy."

Ice packs are often used for cryo therapy. These are placed on the affected shoulder and held in position using compressive wraps or other known techniques. "Gel packs" may be substituted for the ice packs in some applications. Another less common approach is the use of cooled fluid (often water) circulated through a sealed bladder which is placed in contact with the affected area.

The use of ice packs has several known disadvantages. One disadvantage is that the patient's skin must be separated from the ice pack by a layer of appropriately insulating material. This is often required to prevent frost burns. Since the ice pack will remain at 0 degrees Celsius while the phase change from solid to liquid is progressing, it is capable of cooling the patient's skin to a harmful extent. Thus, it is often necessary to use an insulating layer which provides some (but not too much) insulation.

Gel packs alleviate some of the frost burn concern since they generally do not undergo a phase change. The gel pack remains liquid at the temperatures found in most freezers. Thus, when placed on the patient, a gel pack warms up to a more acceptable temperature (well above) degrees Celsius) in a relatively short period of time). Of course, lacking a phase change, the gel pack cannot absorb as much heat as a conventional ice pack.

In addition, both the conventional ice packs and the gel packs are difficult to remove and replace. Such packs must be frequently exchanged for fresh ones in order to make the cryo therapy effective. One set of packs is typically applied to the patient while one or more other sets of packs are cooling in a nearby freezer. The packs on the patient must be exchanged for new ones once they reach an ineffective temperature (typically about 10 degrees Celsius). This process is difficult in the prior art because the compressive wrap used to hold the packs in place must be unwound and then reapplied.

The use of a cooled circulating fluid avoids the frost burn problems present with ice packs and—to a lesser extent—gel packs. However, the bladder in such a system must be connected to a large and bulky cooling unit by an input and output line. This restricts patient mobility. The cooling unit also tends to be noisy, which can disturb patient sleep patterns.

The present invention seeks to eliminate or reduce the problems present in the prior art. It uses replaceable packs containing a suitable cooling mediaum. The preferred cooling medium is one that freezes between about 5 degrees Celsius and about 20 degrees Celsius. Such a medium can absorb considerable heat via the phase change from a solid to a liquid. In addition, such a cooling medium poses little risk of tissue damage (as it will remain at its melting temperature until all the medium has transitioned from a solid to a liquid).

The solid phase of the cooling medium is also significant. It is obviously undesirable for a bag of liquid cooling medium to freeze into a solid block. It is preferable to have the phase change transition into a highly structured crystalline form akin to snow. The bag of frozen cooling medium will then be soft and malleable.

The present invention provides a modular shoulder cooling system using bags of frozen cooling medium. The system facilitates easy exchange of the bags so that the bags can be replaced once their ability to absorb heat is diminished.

BRIEF SUMMARY OF THE PRESENT INVENTION

The present invention comprises a modular shoulder cooling system. A retention panel is affixed over the shoulder. The retention panel is hald in position by a pair of straps attached to a belt around the user's waist. At least a portion of the inward facing surface of the retention panel is covered in loop material.

Bags containing cooling medium are furnished. These are referred to as "cold packs." Each cold pack has a first side with a soft, tactilly pleasing surface. This first surface is intended to face the user. Each cold pack also has a second side intented to face the inward facing surface of the retention panel. This second side includes one or more hook panels configured to engage the loop material on the inward facing surface of the retention panel.

The retention panel includes an upper portion and a lower portion. While the retention panel remains in position on a patient' shoulder, a user can fold the upper portion over the lower portion, thereby exposing the inward facing surface of the retention panel. The user can then attach a cold pack to the upper portion by pressing the hook panel(s) on the cold pack into the loop material on the upper portion. The upper portion is then folded back into its normal position, in which it retains the cold pack on the upper portion of the patient's shoulder.

The same operation can be performed for the lower portion of the retention panel. It may be folded over the upper portion—thereby providing access to remove and/or replace a cold pack on the lower portion. Using this methodology, the cold packs can be easily replaced without removing the retention panel.

Figure 1:
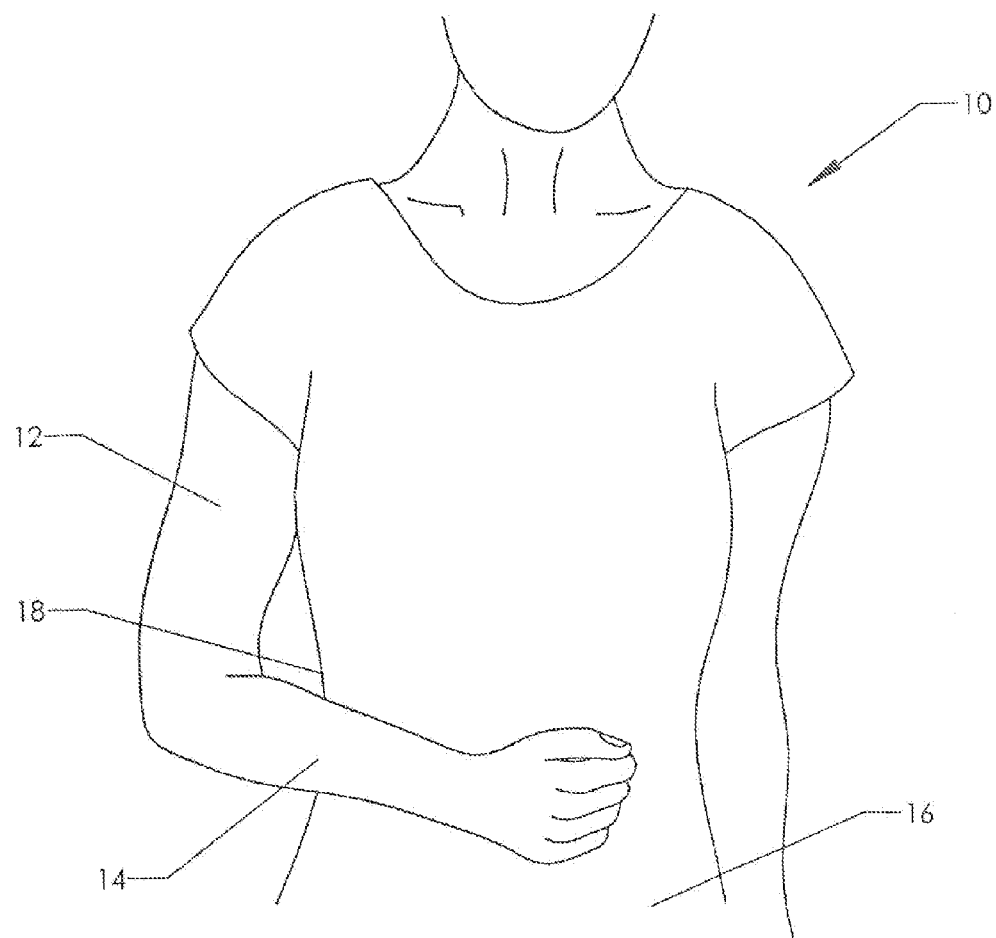
FIG. 1 is a perspective view, showing a patient with her arm positioned to receive a sling.

| REFERENCE NUMERALS IN THE DRAWINGS | | | |
|---|---|---|---|
| 10 | patient | 12 | upper arm |
| 14 | forearm | 16 | waist |
| 18 | lateral chest | 20 | sling |
| 22 | shoulder strap | 24 | clip |
| 26 | release assembly | 28 | belt |
| 30 | female release | 32 | male release |
| 34 | abduction pillow | 36 | hook panel |
| 38 | pad | 40 | neutral axis |
| 42 | external rotation wedge (15°) | 44 | external rotation wedge (30°) |
| 46 | hook panel | 48 | hook panel |
| 50 | hook panel | 52 | hook panel |
| 54 | wedge portion | 56 | front portion |
| 58 | corner | 60 | anterior surface |
| 62 | body relief | 64 | external rotation axis |
| 66 | lateral surface | 68 | lateral surface |
| 70 | lateral mounting surface | 72 | posterior mounting surface |
| 74 | corner | 76 | affected shoulder |
| 78 | opposite arm | 80 | contralateral pad |
| 82 | anchor panel | 84 | pivot |
| 86 | female release | 88 | hook panel |

| REFERENCE NUMERALS IN THE DRAWINGS | | | |
|---|---|---|---|
| 90 | retention panel | 92 | anterior buckle |
| 94 | posterior buckle | 96 | anterior strap |
| 98 | posterior strap | 100 | male release |
| 102 | female release | 104 | hook panel |
| 106 | lower extension leg | 108 | channel |
| 109 | upper extension leg | 110 | connective strap |
| 112 | cold pack | 114 | vent |
| 116 | relief | 118 | hook panel |
| 120 | lower portion | 122 | upper portion |
| 124 | soft surface | 126 | lower edge |
| 128 | upper edge | | |

DETAILED DESCRIPTION OF THE INVENTION

The present invention applies cryo therapy to a patient's shoulder. The application of shoulder cryo therapy is advantageous in a wide variety of situations, including trauma care and post-surgical care. It is commonly used in post-surgical care where other shoulder stabilizing components are present. Thus, the invention is preferably able to work in conjunction with these other components.

FIGS. 1-10 illustrate exemplary shoulder stabilizing components. The present invention is by no means limited to use with the types of other components illustrated. However, as it is beneficial to the reader's understanding to have some knowledge of these other components they will be briefly explained.

FIG. 1 shows patient 10 holding her right arm in a position which is used to stabilize the shoulder joint. She has upper arm 12 positioned proximate lateral chest 18. Forearm 14 is positioned in front of the abdomen, just above waist 16.

Figure 2:
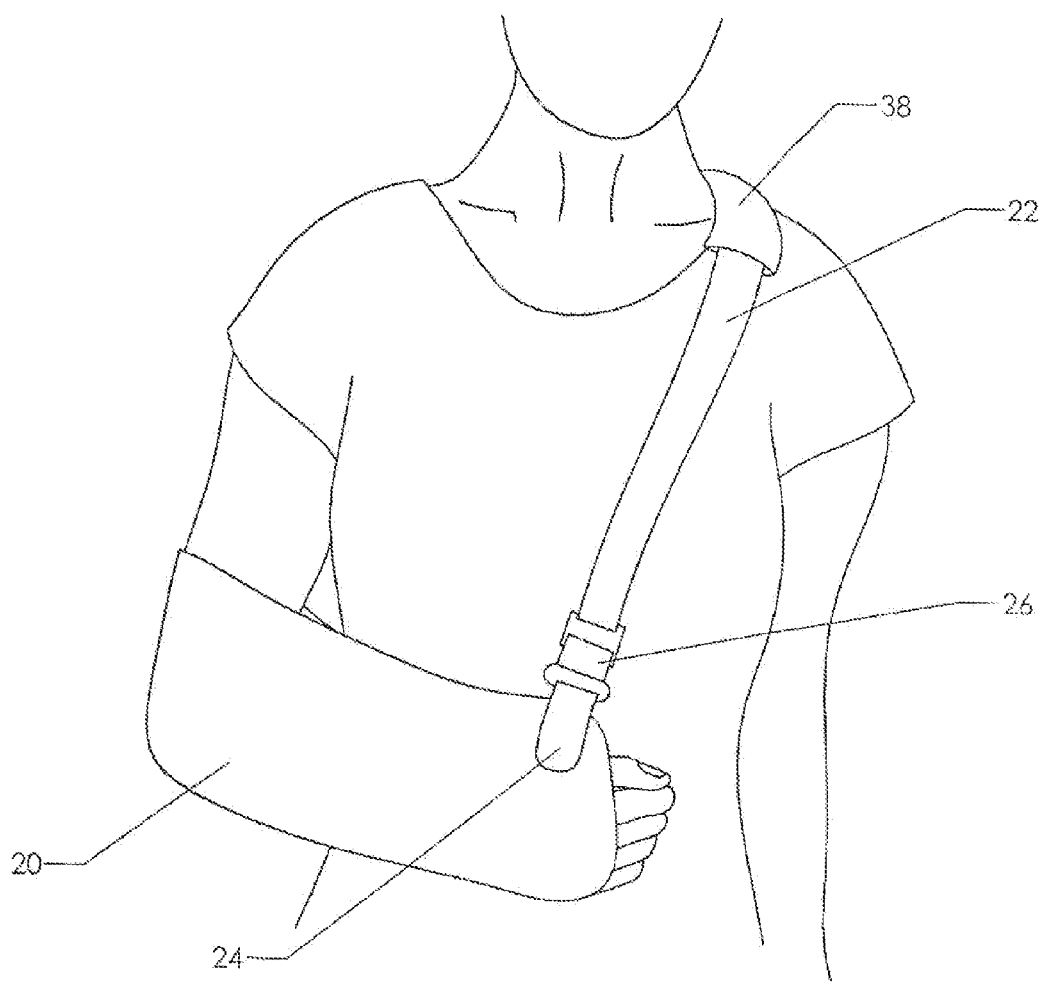
FIG. 2 is a perspective view, showing the patient of FIG. 1 with a sling installed.

FIG. 2 shows the same patient after sling 20 has been placed around her arm. Slings similar to the one shown in FIG. 2 are well known in the art. However, the specific sling illustrated is unique and is therefore not designated "prior art."

The sling is preferably made of a breathable fabric which has a VELCRO loop covering on its exterior. Shoulder strap 22 is connected to a posterior portion of the sling. It passes over the shoulder and connects to sling 20 near the patient's hand. Clip 24 is provided with a VELCRO hook covering so that when it is pressed against the loop covering on the exterior of sling 20 it stays in place. Thus, the user may attach shoulder strap 22 to sling 20 in a suitable position according to the particular patient's anatomy.

Release 26 is preferably a snap-type quick release, where pressing one or more movable portion disengages the connection. This feature allows the patient or practitioner to easily detach and reattach the shoulder strap without shifting the anchor point set by clip 24. Pad 38 is preferably provided to spread the load of the shoulder strap more evenly across the patient's shoulder.

Figure 3:
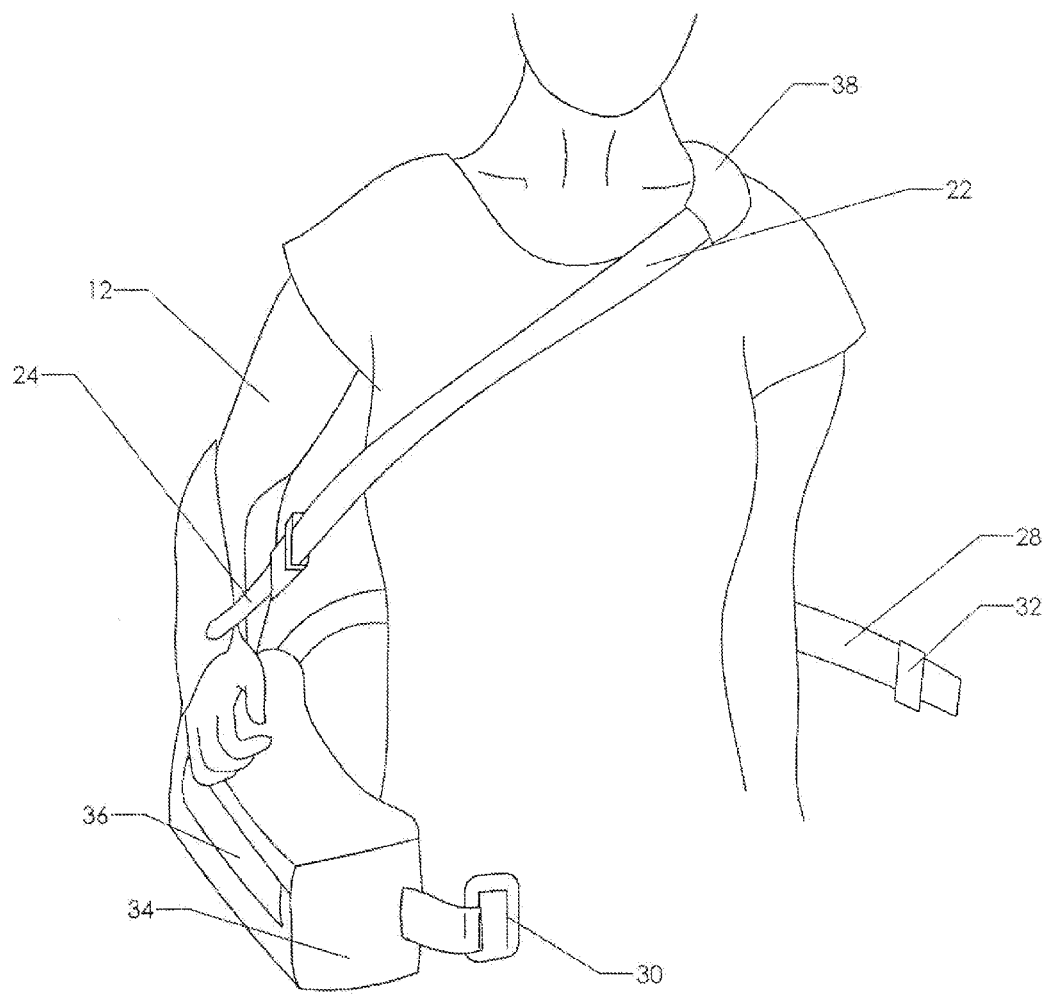
FIG. 3 is a perspective view, showing the installation of an abduction pillow.

For many procedures, it is desirable to abduct the shoulder joint to some extent prior to immobilizing it. Returning to FIG. 1, abducting the shoulder joint generally refers to pivoting upper arm 12 away from lateral chest 18. FIG. 3 shows a device which is commonly used for this purpose. Abduction pillow 34 is attached to the patient by circling belt 28 around the patient's waist. Male release 32 is then snapped into female release 30.

Once the patient's arm is properly positioned, the user presses the sling against the abduction pillow. Hook panel 36 then engages the VELCRO loop covering on the outward facing surfaces of the sling and holds the sling and abduction pillow in the desired position.

Figure 4:
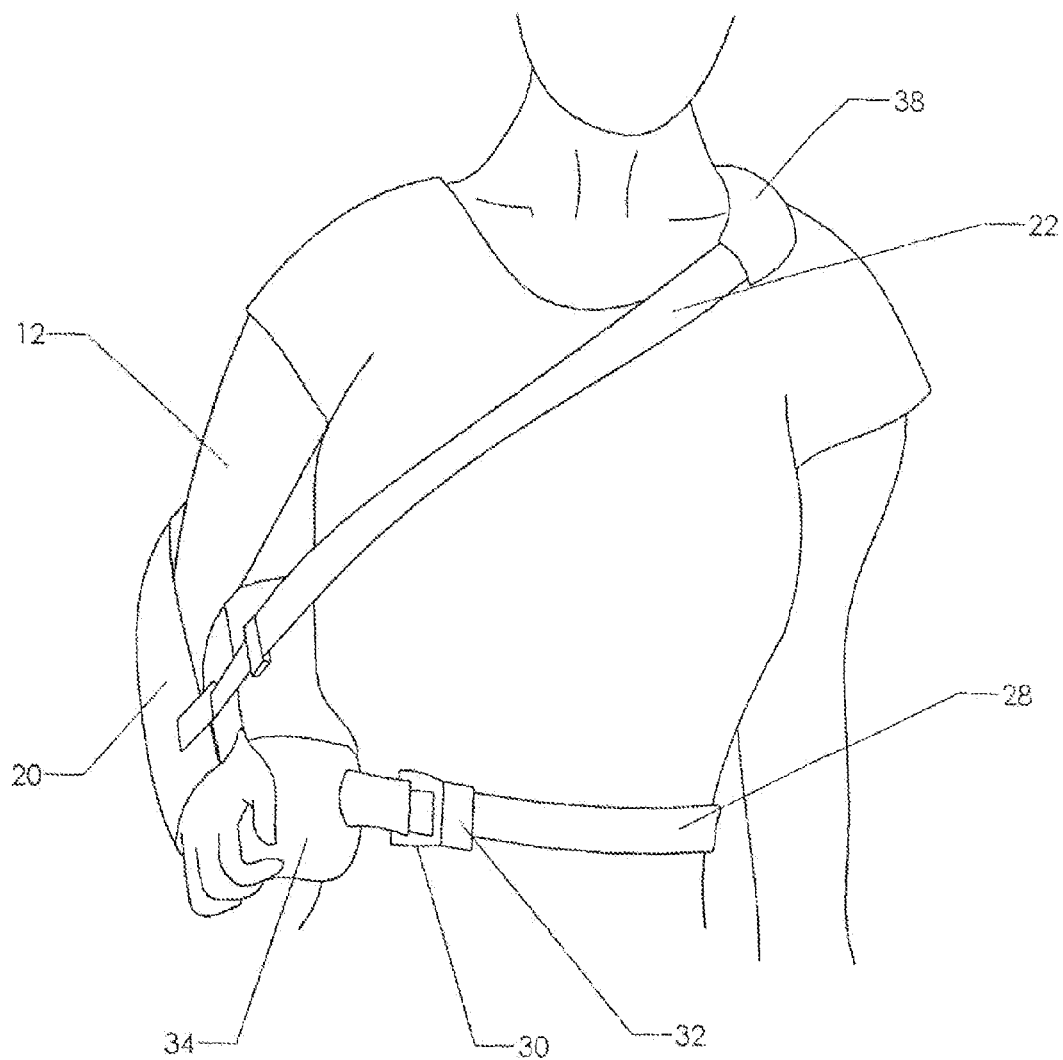
FIG. 4 is a perspective view, showing the abduction pillow in an installed position.
Figure 5:
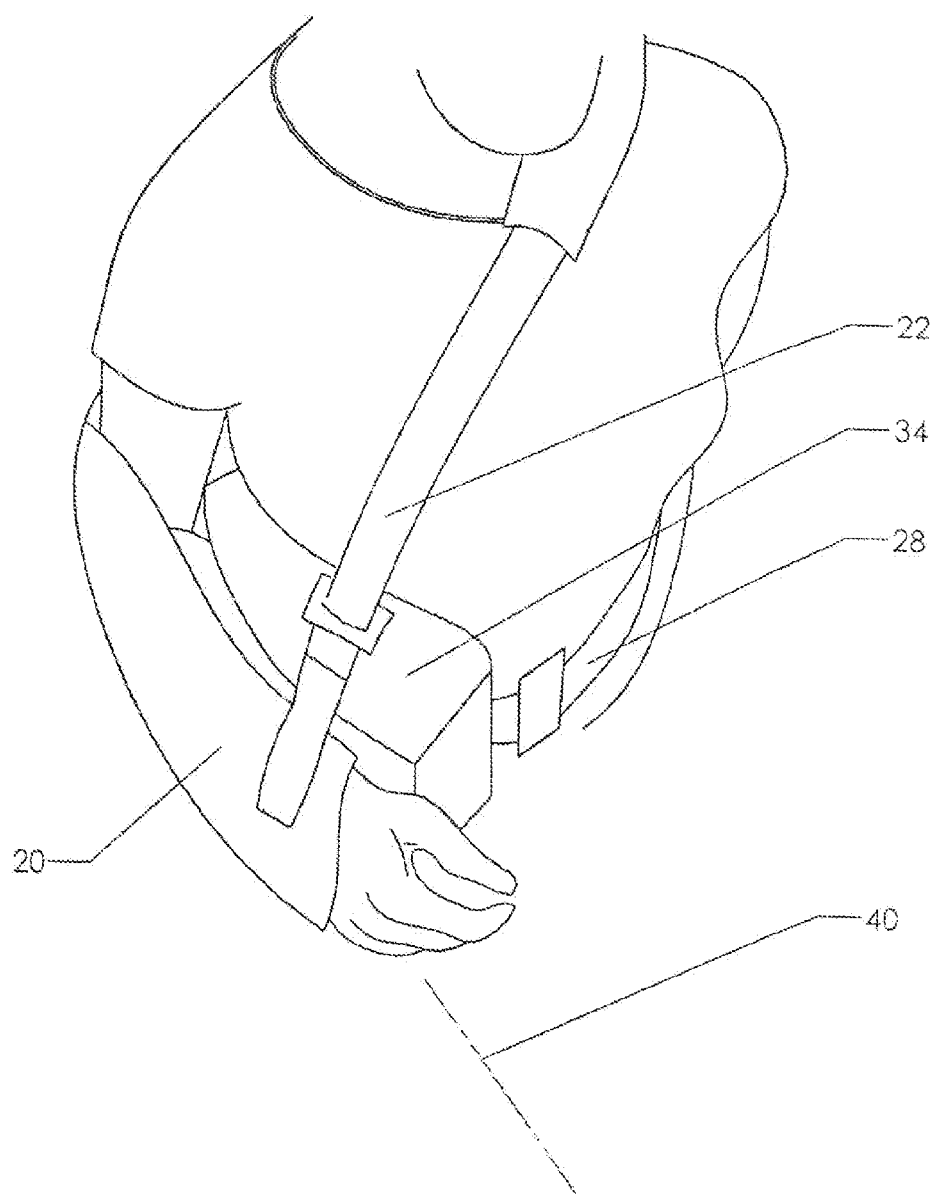
FIG. 5 is a perspective view, showing the same configuration as FIG. 4 from an elevated perspective looking downward.

FIG. 4 shows the installed abduction pillow 34 and sling 20. The position shown is considered to be a "neutral" position. The shoulder joint is abducted somewhat (pivoted outward) but is not rotated internally or externally. FIG. 5 shows the same assembly from a raised position looking downward. Neutral axis 40 is shown extending outward along the approximate centerline of the patient's forearm.

FIG. 5 shows the patient's shoulder joint in a stabilized position. Sling 20 is attached to abduction pillow 34, which is attached to the patient via belt 28. Shoulder strap 22 supports the forward portion of the sling, proximate the patient's wrist. The use of hook-and-loop (VELCRO) fasteners to join the sling to the abduction pillow allows the sling to be properly positioned despite a wide variation in patient anatomy. The use of the release assemblies on belt 28 and shoulder strap 22 also allows the device to be easily installed and removed without altering its adjusted position.

FIG. 5 shows an orientation in which the user's forearm is roughly aligned with neutral axis 40. The shoulder joint is abducted somewhat—meaning that the upper arm is pivoted outward with respect to the lateral chest wall. However, no external rotation has been applied. The term "external rotation" is defined with respect to the upper arm, the forearm, and the elbow. External rotation is created by keeping the upper arm and elbow in the same position while moving the wrist outward away from the body. This motion externally rotates the shoulder joint.

Figure 6:
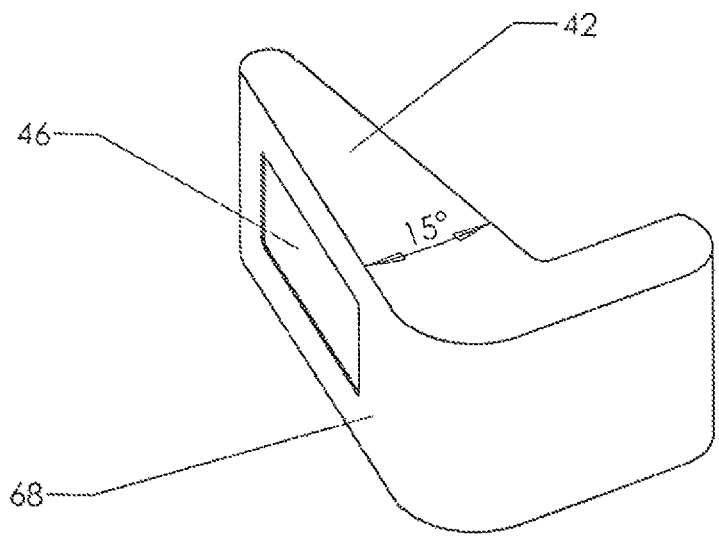
FIG. 6 is a perspective view showing two external rotation wedges.
Figure 6:
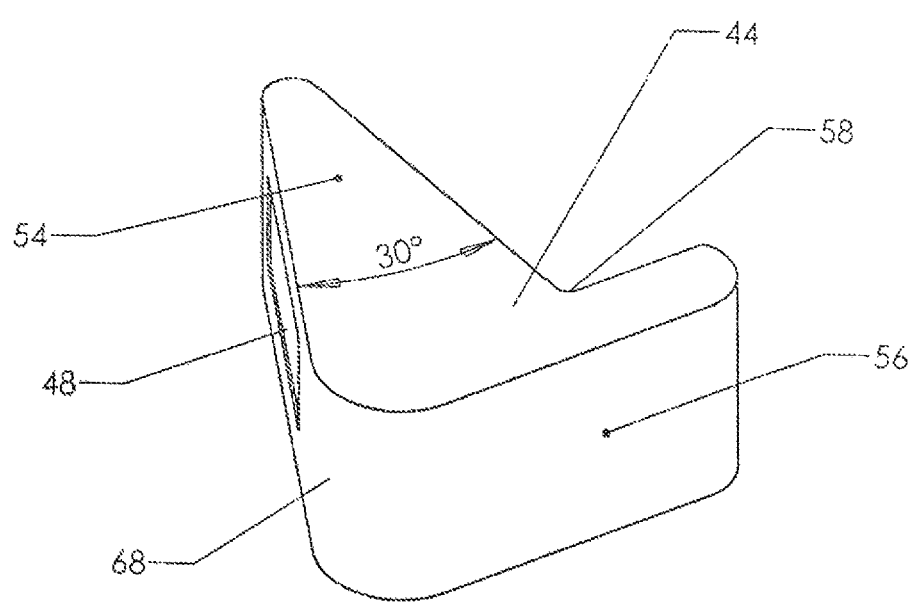
Figure 7:
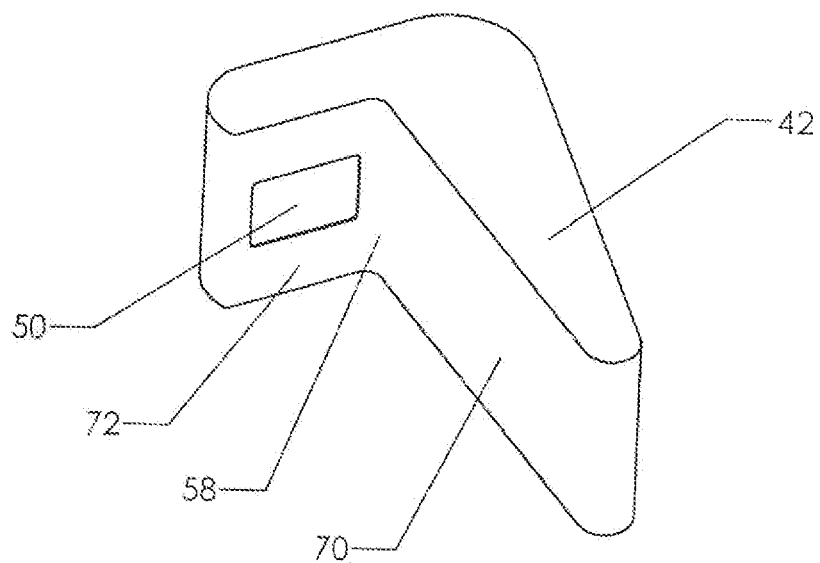
FIG. 7 is a perspective view showing the external rotation wedges of FIG. 6 from a different vantage point.
Figure 7:
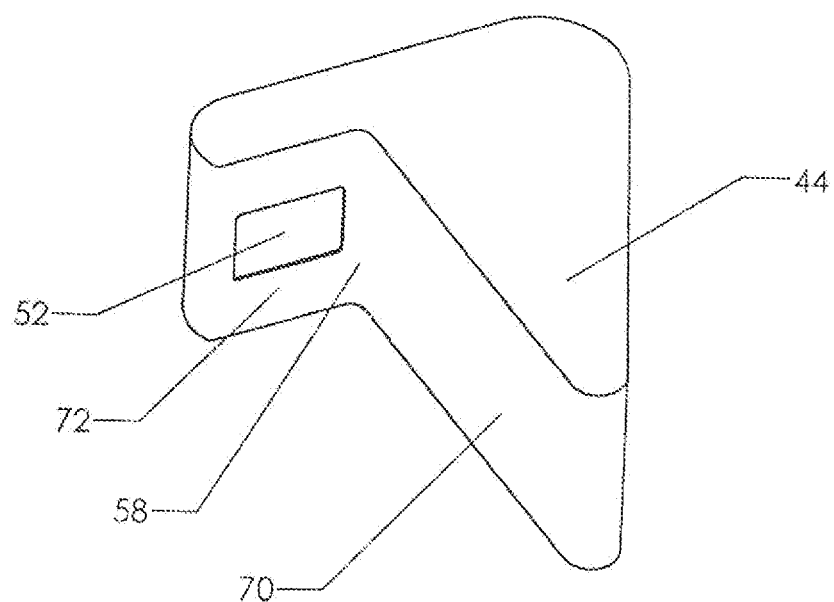

FIG. 5 shows the patient's wrist in the neutral position (lying on neutral axis 40). If the wrist is moved toward the waist then internal rotation is produced. If the wrist is moved outward then external rotation is produced. FIGS. 6 and 7 depict a pair of external rotation wedges used to create a desired degree of external rotation. These wedges are designed to be added to the abduction pillow. It is preferable to provide a plurality of external rotation wedges with differing amounts of angular offset. External rotation wedge 42 provides 15 degrees of external rotation whereas external rotation wedge 44 provides 30 degrees of external rotation.

Each external rotation wedge includes a lateral surface 68. This lateral surface includes a hook panel (hook panel 46 for the upper rotation wedge and hook panel 48 for the lower one). Wedge portion 54 includes a fixed angular displacement. Front portion 56 faces forward. The wedge is roughly in an "L" shape when viewed from above—with the two portions joining at corner 58.

FIG. 7 shows the same pair of external rotation wedges from the opposite side. Posterior mounting surface 72 is intended to face toward the rear, while lateral mounting surface 70 is intended to face toward the side of the patient. Each posterior mounting surface 72 includes a hook panel (hook panel 50 on the upper wedge and hook panel 52 on the lower wedge). Corner 58 is formed by the intersection of the posterior mounting surface and the lateral mounting surface. The lateral mounting surface is preferably covered with loop material.

The angle between lateral mounting surface 70 and lateral surface 68 (shown in FIG. 6) defines the degree of external rotation provided by the particular wedge. The angular displacement between these surfaces is 15 degrees for the wedge shown at the top of the view. The angular displacement is 30 degrees for the wedge shown at the bottom of the view. A variety of angular displacements are preferably provided so that a physician or physical therapist is able to select the right amount for each particular patient.

Figure 8:
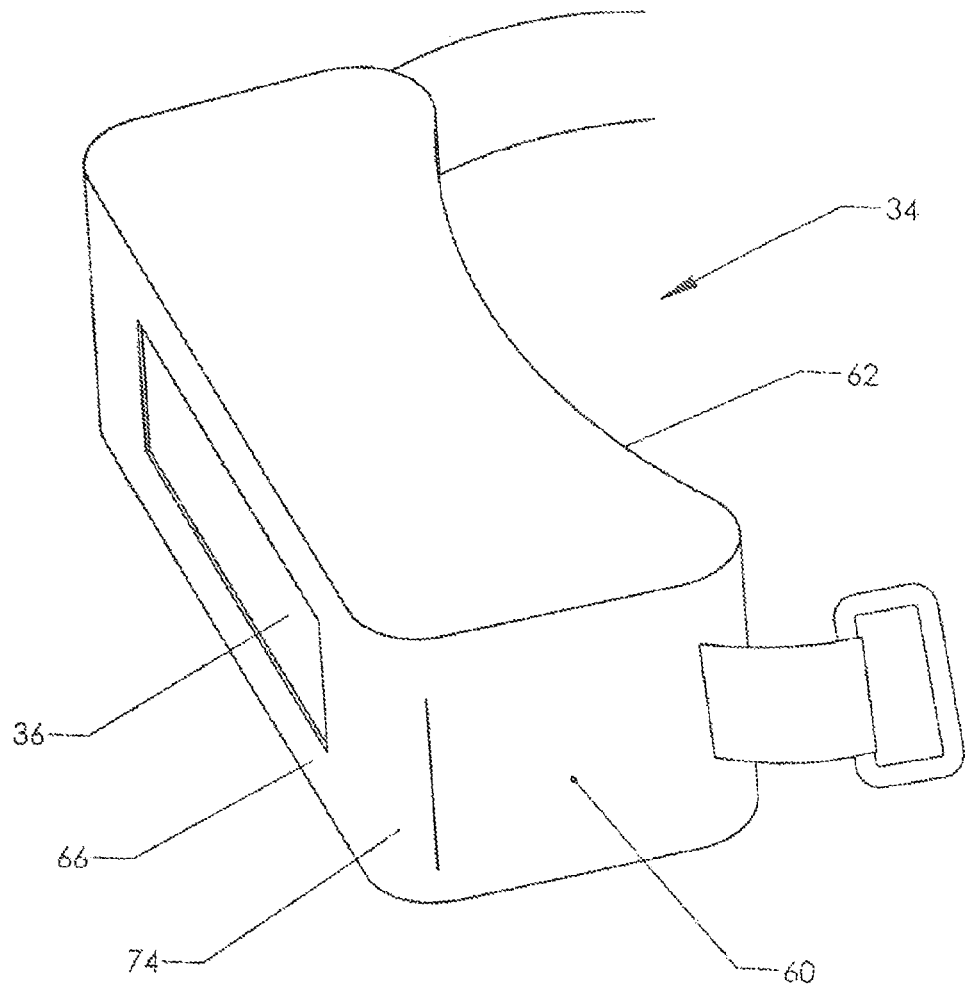
FIG. 8 is a perspective view, showing the abduction pillow of FIGS. 4 and 5 in more detail.

FIG. 8 shows a detailed perspective view of abduction pillow 34. Body relief 62 is provided to conform the pillow to the user's side. The inward facing surface (not shown) is preferably provided with a material which holds the pillow in position. Anterior surface 60 is preferably covered in loop material. Lateral surface 66 includes a hook panel 36. Corner 74 is formed by the intersection of anterior surface 60 and lateral surface 66.

Returning now to FIG. 7, an external rotation wedge is designed to attach to the abduction pillow by mating corner 58 on the wedge with corner 74 on the abduction pillow. The external rotation wedges are preferably made of pliable material (such as a fabric covered foam) so that the user can bend the two legs of the "L" outward. The user then presses corner 58 against corner 74 and presses the two legs back inward. The loop covering on lateral mounting surface 70 engages hook panel 36 on abduction pillow 34. Likewise, hook panel 52 on the abduction wedge engages the loop covering on anterior surface 60 on the abduction pillow.

Figure 9:
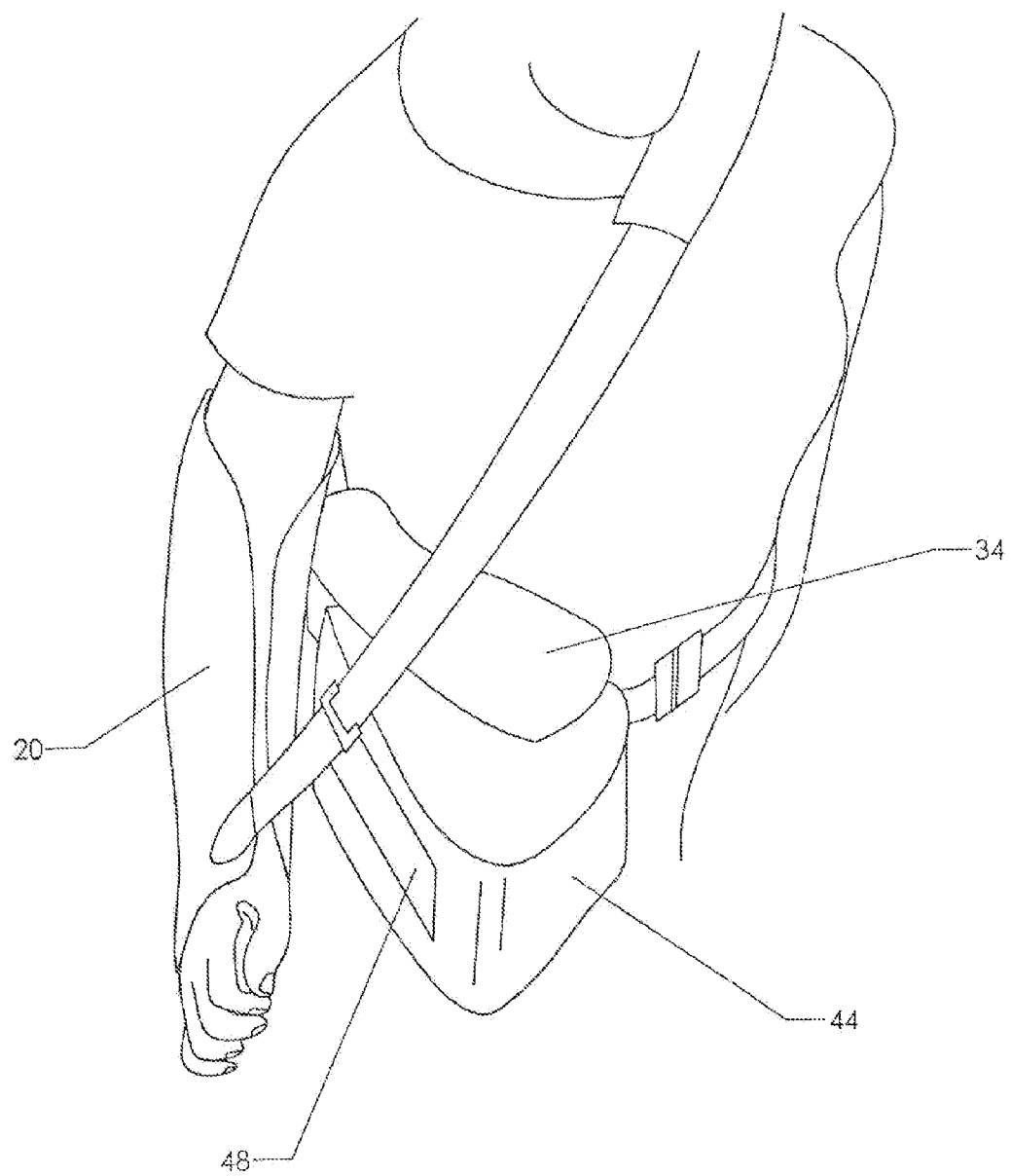
FIG. 9 is a perspective view, showing the installation of an external rotation wedge on an abduction pillow.

FIG. 9 shows external rotation wedge 44 (having 30 degrees of angular displacement) installed on abduction pillow 34. The reader will observe how hook panel 48 faces outward toward sling 20. The sling is covered in loop material so that when the sling is pressed inward against hook panel 48 it will become attached to the external rotation wedge.

Figure 10:
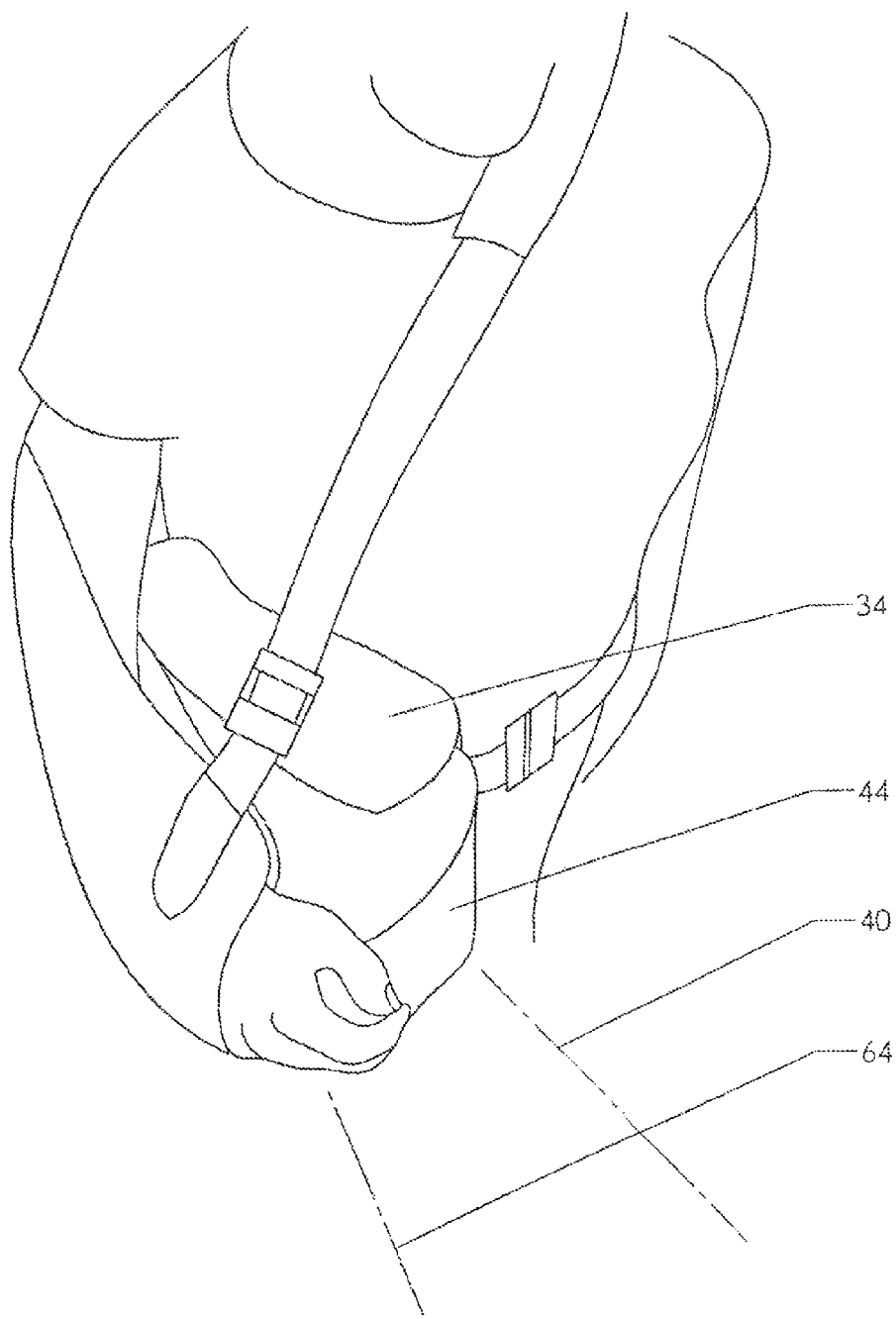
FIG. 10 is a perspective view, showing the complete assembly of the abduction pillow, the external rotation wedge, and the sling.

FIG. 10 shows the patient after the sling has been attached to the abduction pillow. The external rotation wedge has rotated the forearm outward so that the centerline of the forearm (external rotation axis 64) is rotated well away from neutral axis 40.

The present invention is preferably able to function without disturbing the function of components such as those illustrated in FIG. 10. Accordingly, it is best to design it to fit over the existing components (though it could certainly be designed in other ways as well).

Figure 11:
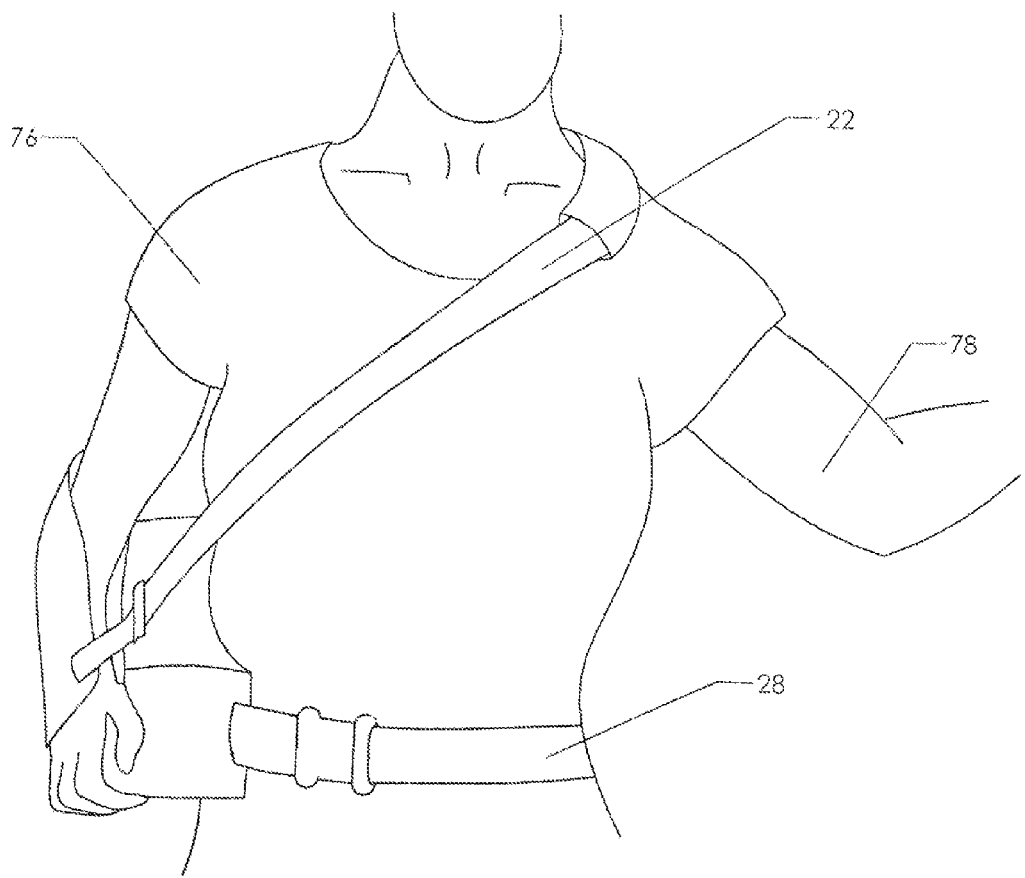
FIG. 11 is a perspective view, showing a patient with her opposite (non-affected) arm raised.

FIG. 11 shows a front view of the patient with a belt and abduction pillow installed (but in this case with no external rotation wedges). It is desirable to apply cryo therapy to affected shoulder 76. The cryo therapy device should be attached to the patient. One way to do this is to attach the cryo therapy device to belt 28 beneath opposite arm 78 ("opposite" meaning the arm that it not attached to the affected shoulder).

Figure 12:
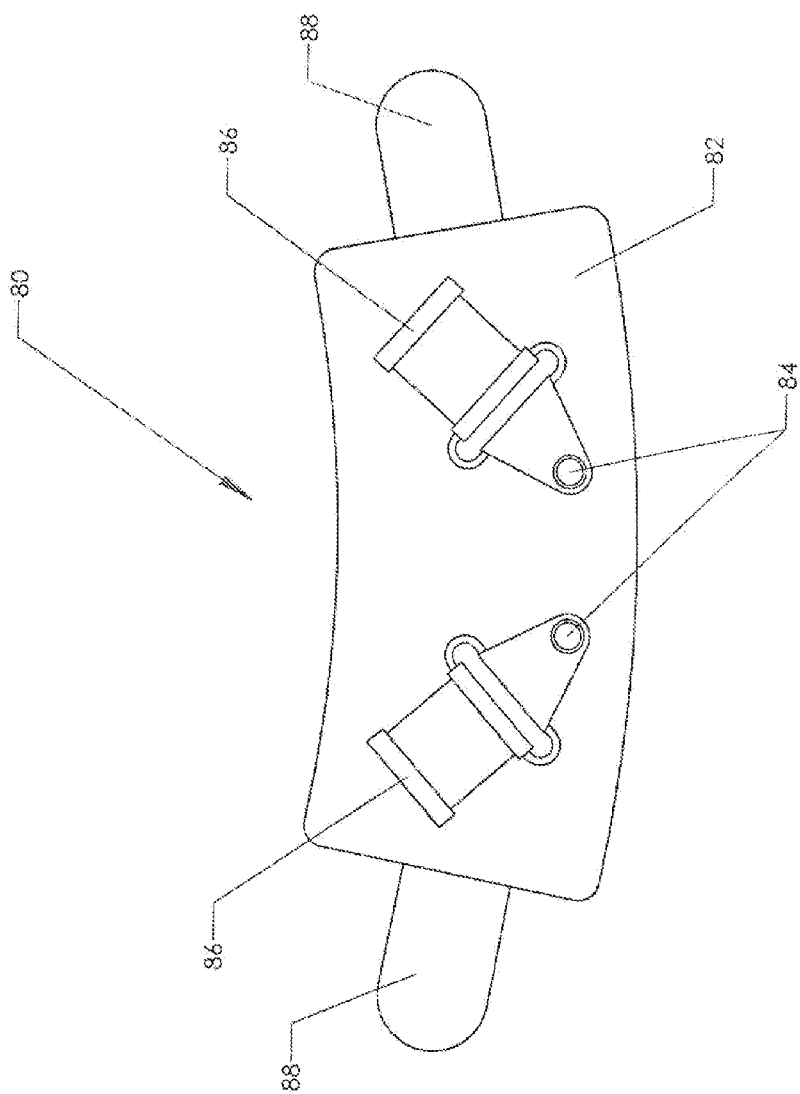
FIG. 12 is an elevation view, showing a contralateral pad.

Attachment features can be provided as part of belt 28. As cryo therapy will not always be used, however, it is preferable to make the attachment features removable. FIG. 12 shows contralateral pad 80, which includes the attachment features. The contralateral pad has hook panel 88 across its width and extending a short distance out the lateral sides. (The hooks face away from the viewer in FIG. 12). Hook panel 88 contains hook features facing away from the viewer in FIG. 12. The belt beneath opposite arm 78 contains an outward-facing loop covering. Thus, when contralateral pad 80 is pressed into the belt hook panel 88 will engage the loop covering and retain the contralateral pad in position.

Two female releases 86 are attached to anchor panel 82 via pivots 84. These female releases are part of a quick-release system that allows a user to attach and detach straps to the contralateral pad. A quick-release is any one of a number of configurations that allows the user to unlatch the release assembly by pressing on a portion or portions thereof.

Figure 13:
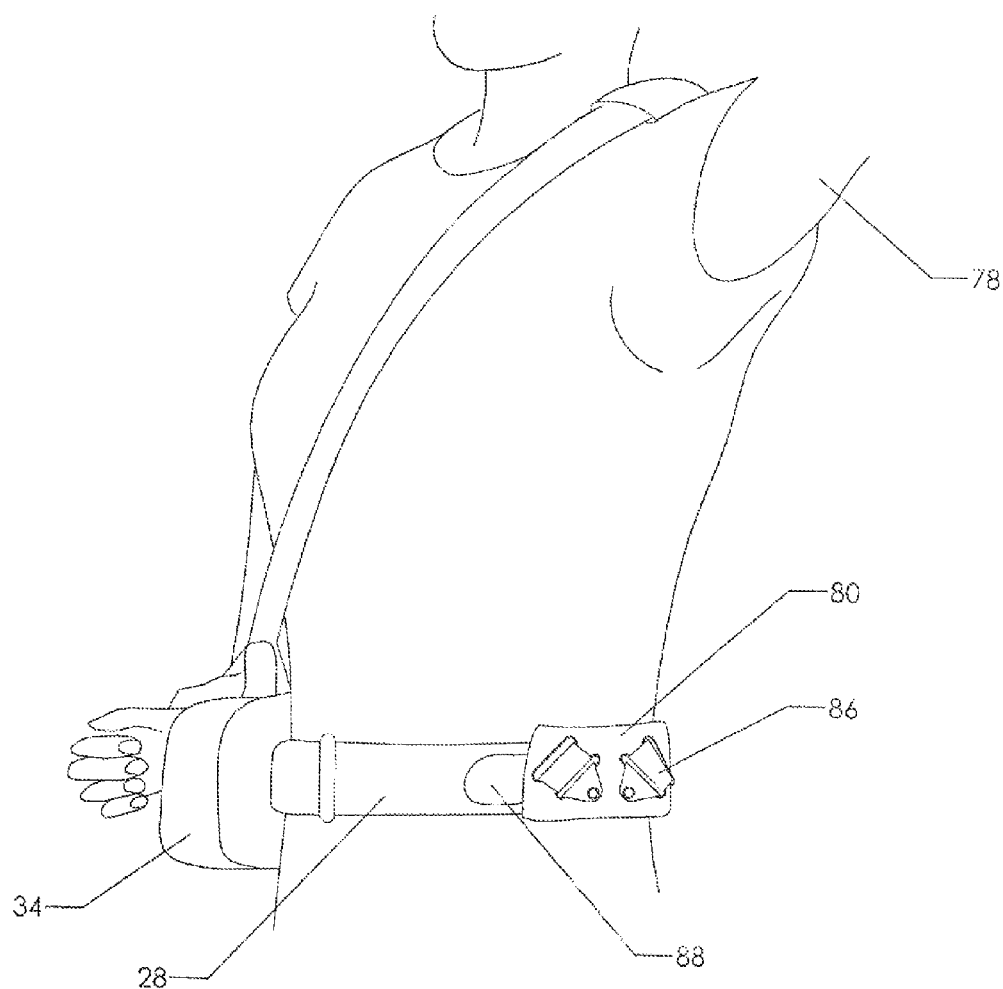
FIG. 13 is a perspective view, showing the contralateral pad installed on a belt.
Figure 14:
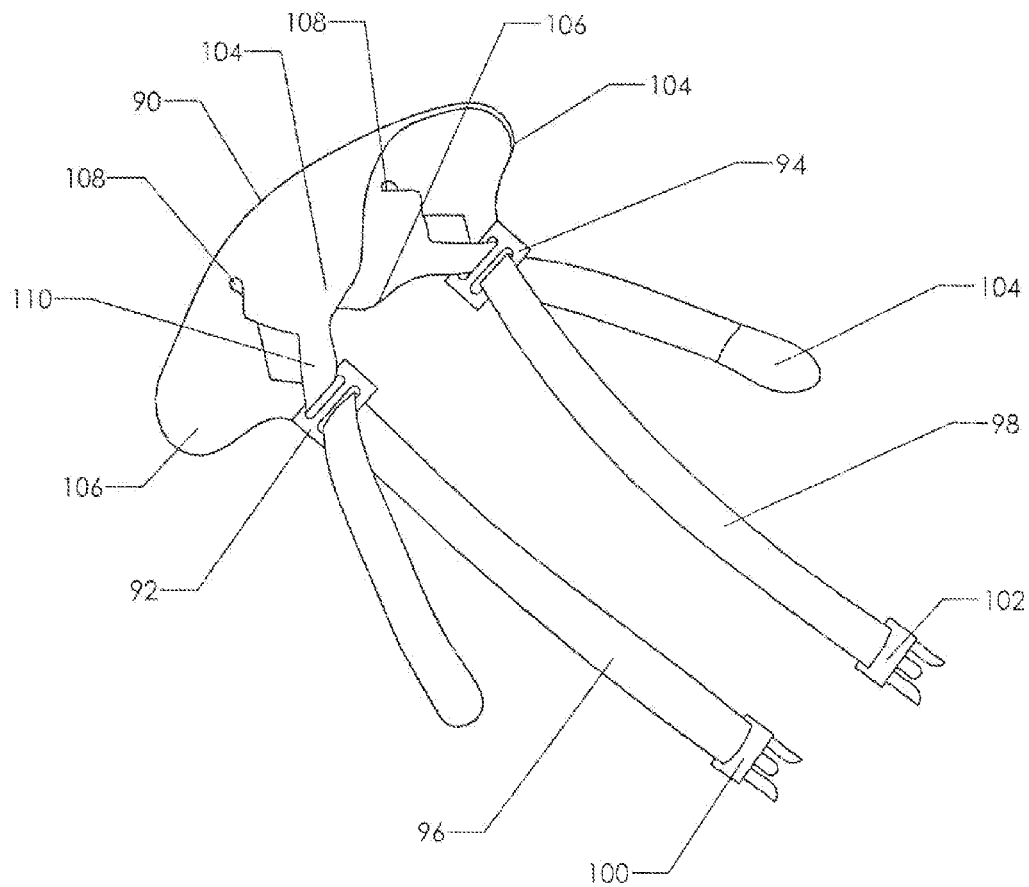
FIG. 14 is a perspective view, showing a retention panel and its associated mounting straps.

FIG. 13 shows contralateral pad 80 installed on belt 28 beneath opposite arm 78. Hook panel 88 is locked into the loop covering on the exterior of belt 28 to maintain the desired position. FIG. 14 shows the device which actually applies the cryo therapy to the shoulder. Retention panel 90 is intended to press inward against the affected shoulder. It has an inward facing surface intended to bear against the shoulder. This inward facing surface is preferably provided with loop covering.

In order to conform to the curved shape of the human shoulder the retention panel is preferably divided into two sections split by channels 108. Lower extension legs 106 lie on one side of the channel while upper extension legs 109 lie on the other. Each pair of upper and lower extension arms is joined by a connecting strap 110. The connecting strap 110 closest to the viewer in FIG. 14 passes through anterior buckle 92. The connecting strap that is farthest from the viewer passes through posterior buckle 94.

The retention panel must be attached to the patient so that it remains in the propoer position. One way to accomplish this goal is to use straps. FIG. 14 shows anterior strap 96 passed through anterior buckle 92. One end of the anterior strap includes male release 100. This is configured to snap into one of the female releases 86 on contralateral pad 80.

Posterior strap 98 passes through posterior buckle 94. It includes female release 102, which is also configured to attach to contralateral pad 80. The straps may be adjusted and secured using any suitable hardware. One approach is to provide a hook panel 104 on the free end of each strap (The hook panel on anterior strap 96 is facing away from the viewer in FIG. 14 and is therefore not visible).

The outward facing surfaces of the two straps are preferably provided with a loop covering. It is thus possible to pass the straps through the respective buckles, pull them to the appropriate length, and then press the hook panel on each strap into the loop covering in order to secure the strap in position.

Figure 15:
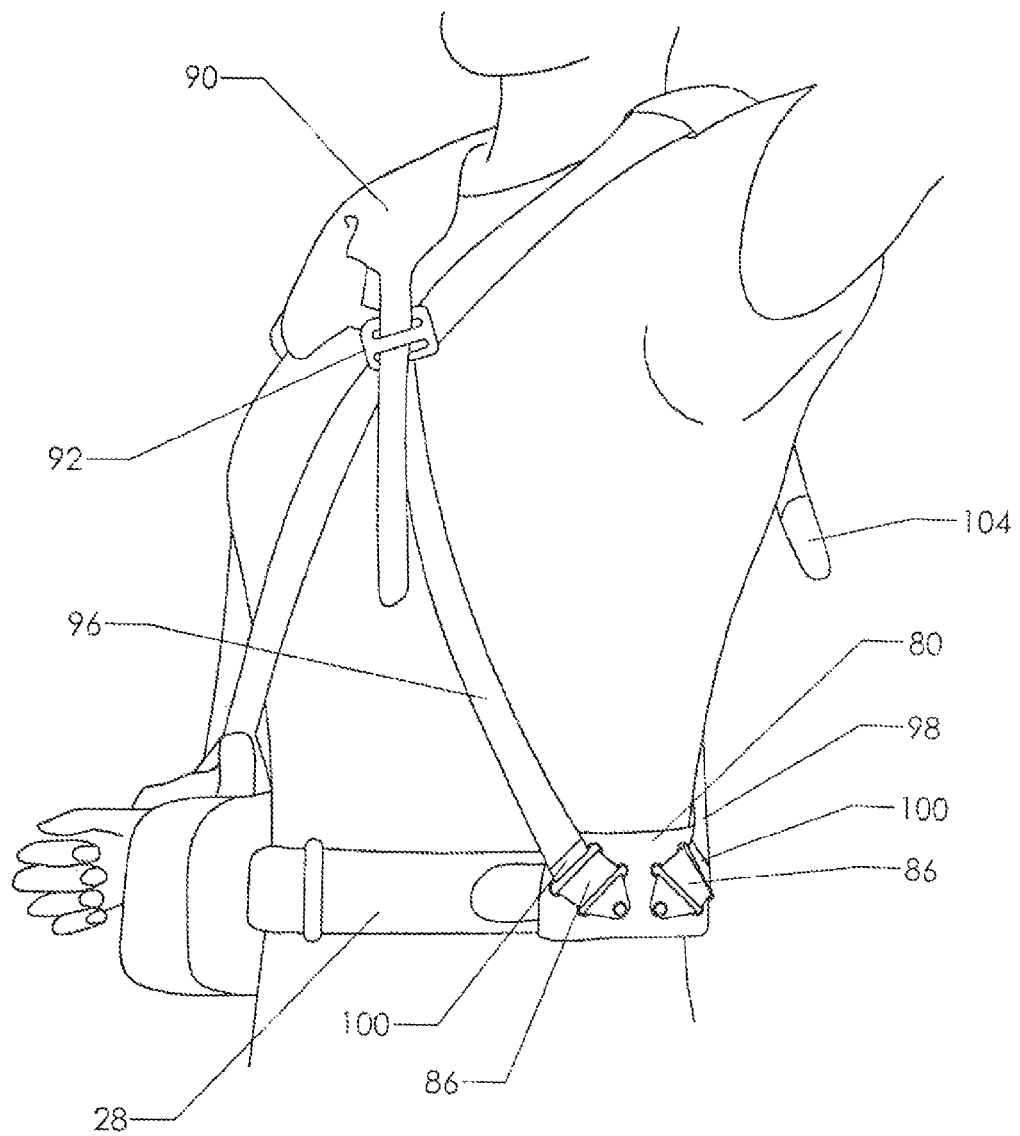
FIG. 15 is a perspective view, showing the retention panel attached to the contralateral pad.
Figure 16:
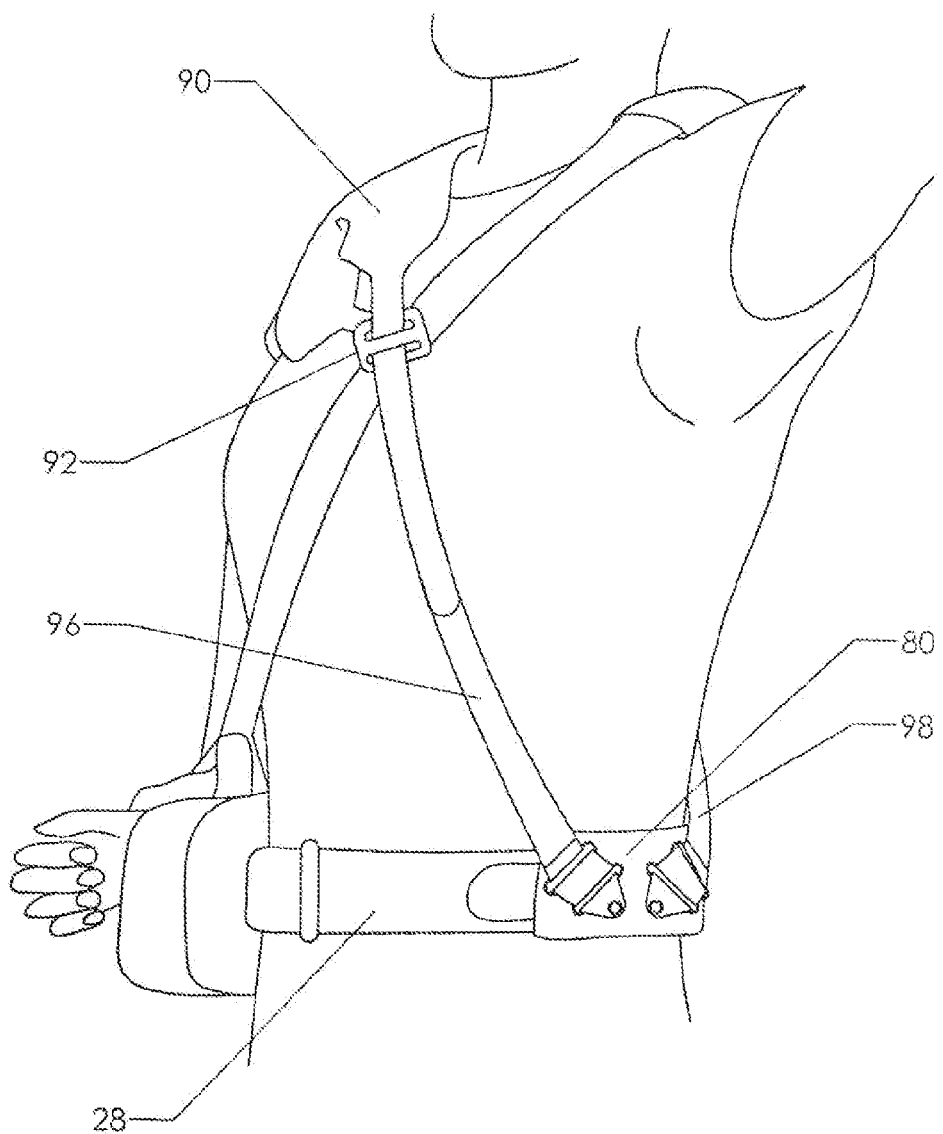
FIG. 16 is a perspective view, showing the retention panel attached to the contralateral pad.

FIGS. 15 and 16 show these steps. In FIG. 15, anterior strap 96 and posterior strap 98 have each been connected to contralateral pad 80. Once retention panel 90 and the securing straps are in position, the user can grasp the free ends of the two straps and pull them toward the contralateral pad.

It is preferable to provide an elastic element in the straps so that they can elongate to some extent. Once the desired amount of tension is achieved, the user presses the hook panel 104 on each strap against the loop covering on the opposite side of each strap. FIG. 16 shows the assembly with the two straps fixed in position. The retention panel is thereby properly positioned on the affected shoulder.

Figure 17:
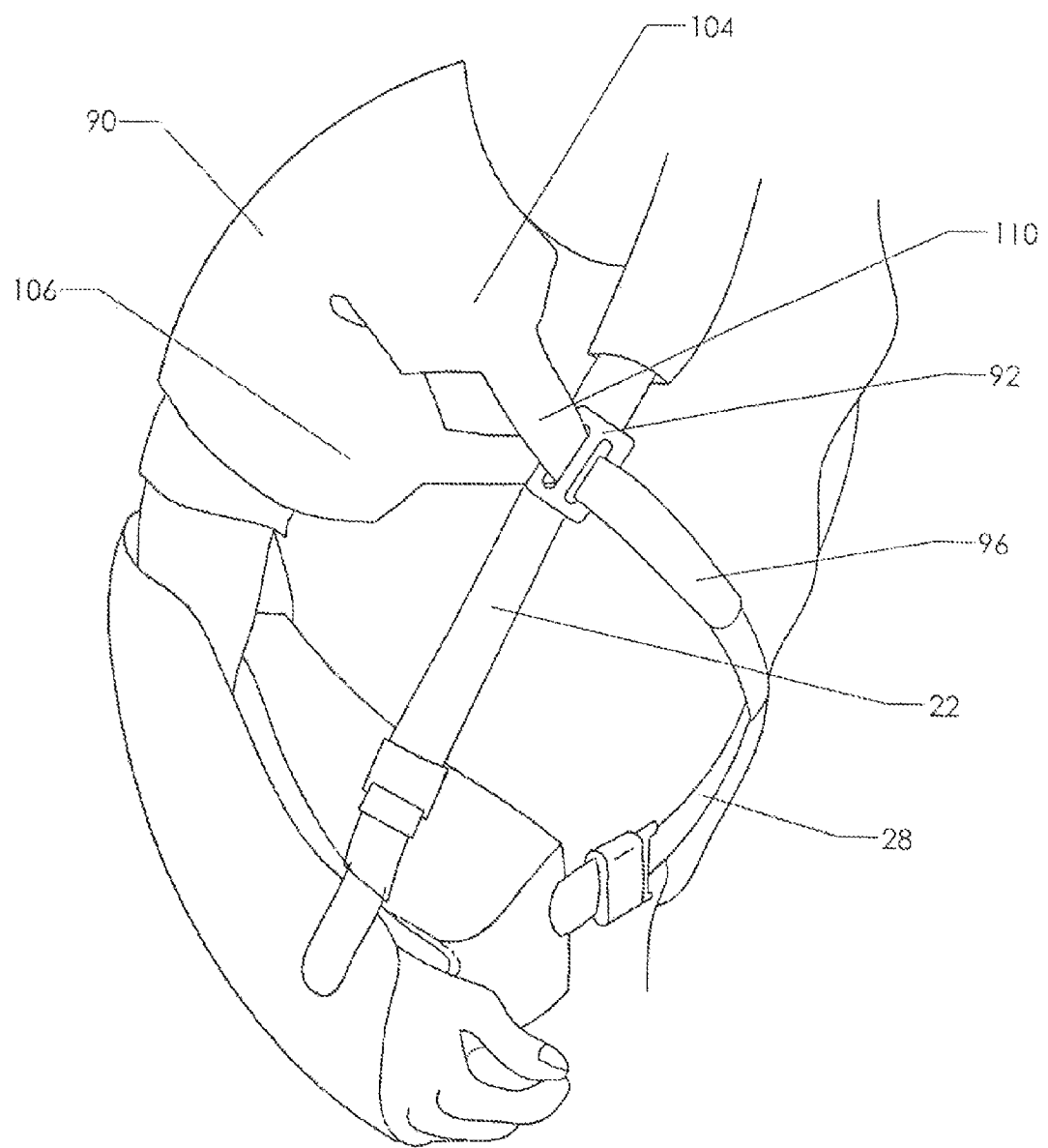
FIG. 17 is a perspective view, showing the retention panel in position from an elevated vantage point.

FIG. 17 shows retention panel 90 lying over the affected shoulder. The reader will note how the anterior lower leg extension 106 and upper leg extension 109 overlap each other—thereby allowing the retention panel to conform to the curved shape of the shoulder. Connector strap 110 slides freely through anterior buckle 92 in order to evenly distribute the tension supplied by anterior strap 96.

The reader will also observe how the cryo therapy devices lie over the top of the shoulder stabilizing hardware (shoulder strap 22, etc.). Thr cryo therapy devices do not interfere with the function of the other devices.

Figure 18:
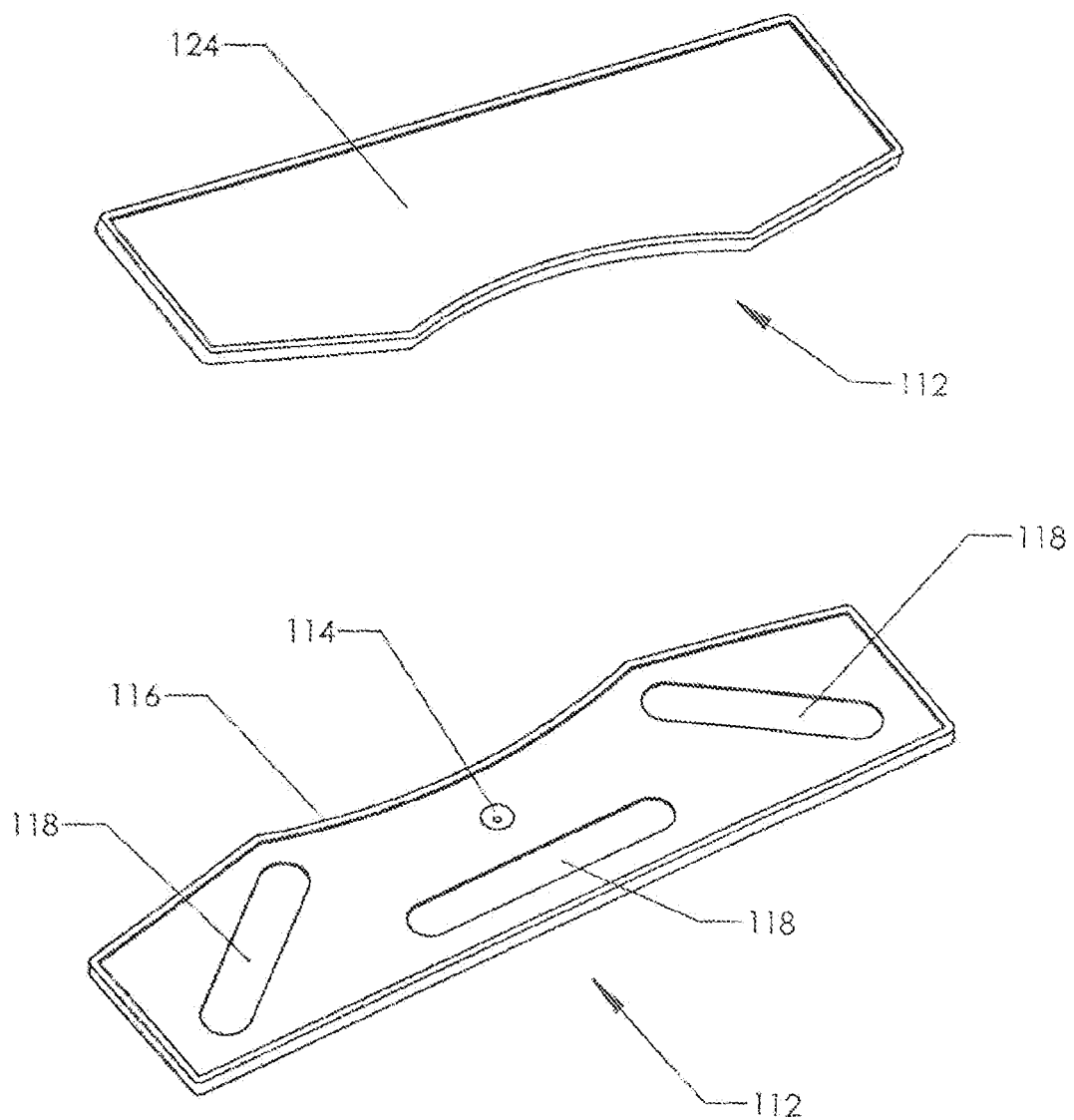
FIG. 18 is a perspective view, showing a pair of cold packs.

As stated previously, a cryo therapy system preferably includes the ability to exchange expended "cold packs" for fresh ones. FIG. 18 shows the type of cold pack which is preferred for the present invention (though the invention will function with many different types of cold packs). Two cold packs 112 are shown in the view. Each cold pack has two sides. The first side preferably includes a smooth fabric covering that is intended to face toward the user's shoulder. The second side faces away from the user and is intended to face toward the inward facing surface of the retention panel.

The cold pack 112 at the top of FIG. 18 has its first side facing upward (soft surface 124). The cold pack 112 at the bottom of FIG. 18 has its second side facing upward. The second side includes one or more hook panels 118. These hook panels are configured to engage the loop covering on the inward facing surface of the retention panel.

Each cold pack 112 also preferably contains a vent 114. As stated previously, the preferred embodiment of the cold pack uses a cooling medium which freezes in a random crystalline structure similar to snow. When the freezing is occurring the cooling medium expands substantially and bulges the cold pack outward (like a pillow). Vent 114 allows ambient air to enter the cool pack so that it can more freely expand.

When the cool pack is applied to the shoulder, heat from the patient's body melt's the frozen cooling medium and it gradually transitions back to a liquid. Vent 114 then allows some of the air within the cold pack to escape so that the cold pack collapses into a flat state. The vent is designed to prevent any leakage of the cooling medium itself.

The cold packs can be made in any suitable shape. For example, it may be desirable to provide arcuate relief 116 so that the pack may more easily rest proximate the neck.

Figure 19:
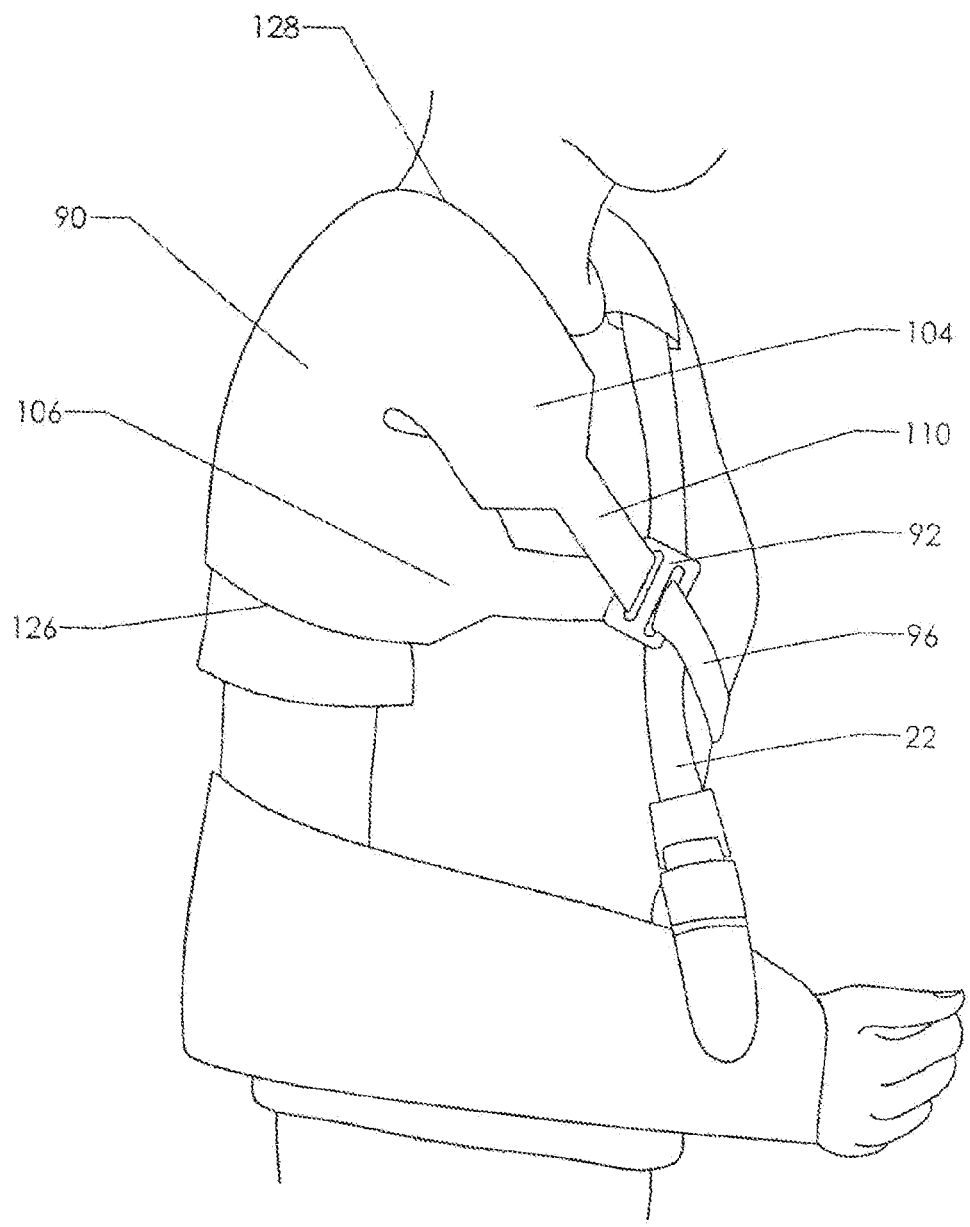
FIG. 19 is a perspective view, showing the retention panel from the side of the affected arm.

Now that the retention panel and the cold packs have been explained in detail, the method of using the invention will be discussed. FIGS. 19-23 illustrate this process. FIG. 19 shows retention panel 90 in place on the affected shoulder of a patient. Retention panel 90 has lower edge 126 on its lower extreme and upper edge 128 on its upper extreme.

Figure 20:
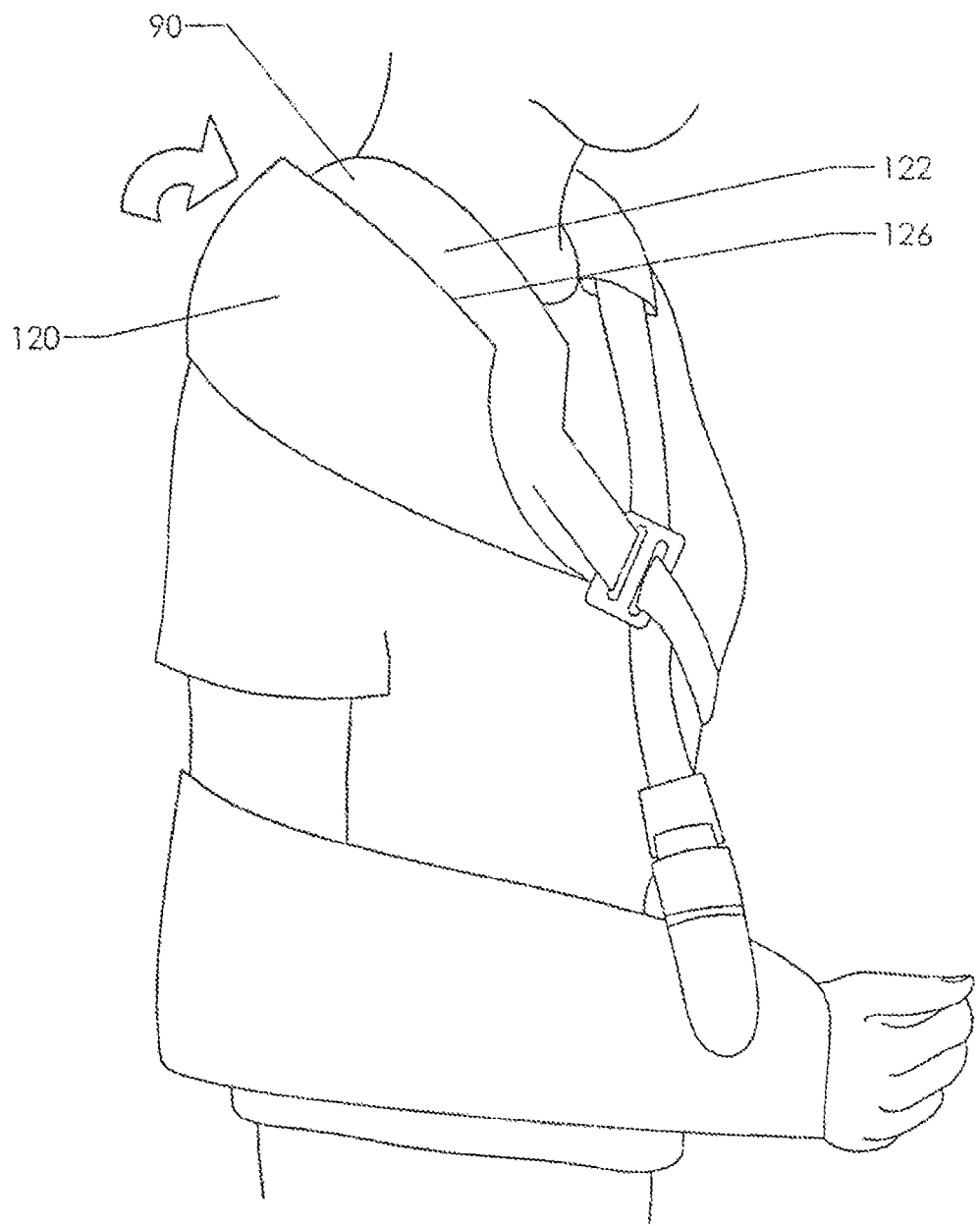
FIG. 20 is a perspective view, showing the lower portion of the retention panel being folded upward.

In order to install a cold pack, a user grasps lower edge 126 and flips it upward as shown in FIG. 20. This action exposes the loop covering on the inward facing surface of the retention panel. The retention panel may be thought of as being divided into two portions (lower portion 120 and upper portion 122). Lower edge 126 is folded over upper portion 122. The retention panel preferably remains in the folded state shown without a user having to hold it there.

Figure 21:
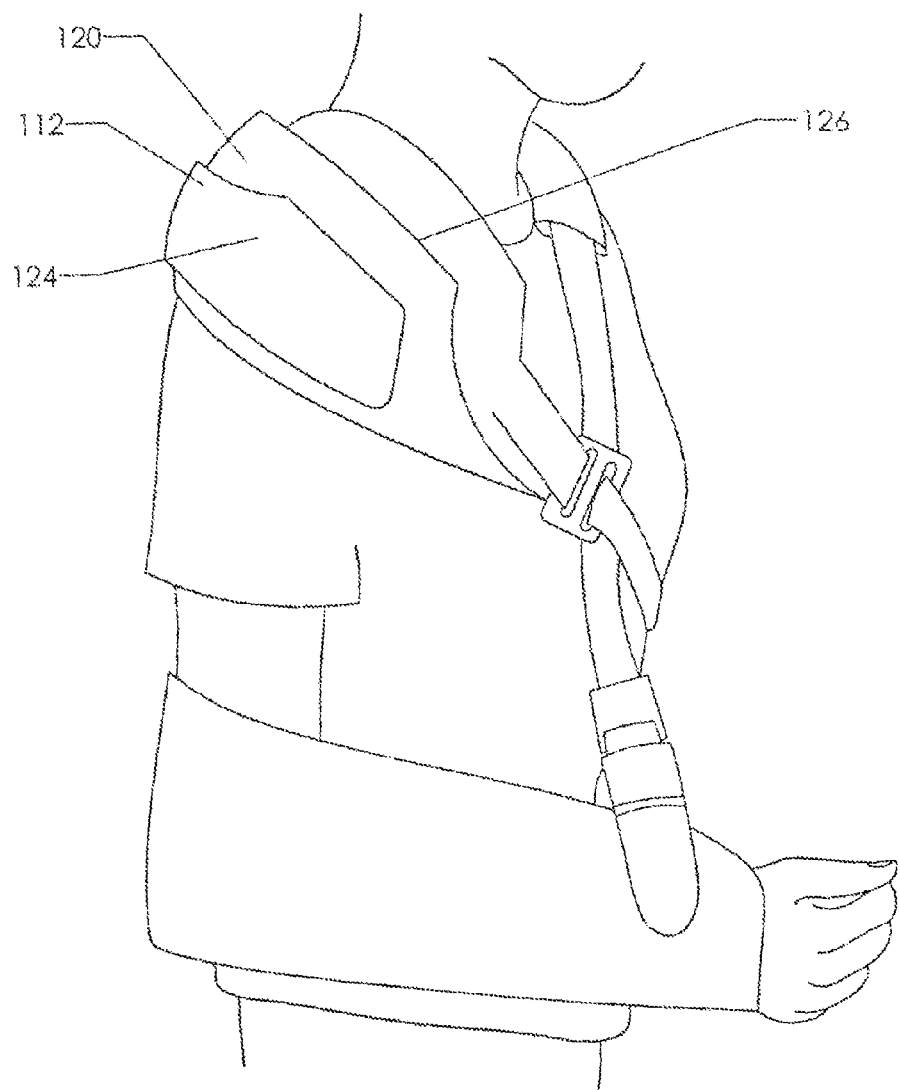
FIG. 21 is a perspective view, showing the placement of a cold pack.

In FIG. 21, the user has pressed a cold pack 112 (with the hook panels facing inward) against the loop covering on lower portion 120. Soft panel 124 is facing outward in the configuration shown. Once the cold pack is secured, the user flips lower edge 126 back to its starting position. The cold pack is thereby inverted and placed against the patient.

Figure 22:
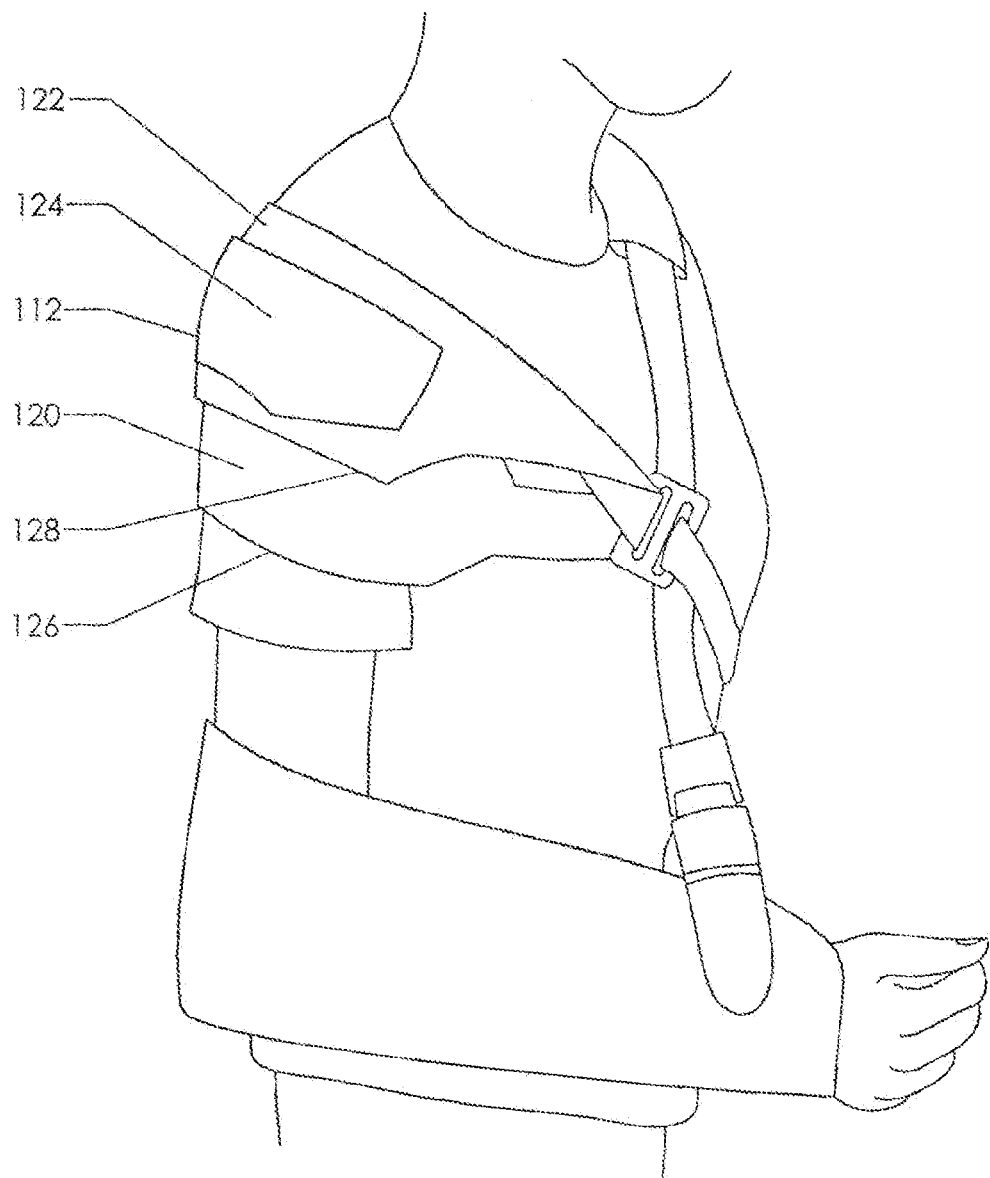
FIG. 22 is a perspective view, showing the placement of a cold pack.

FIG. 22 shows the same process being performed for upper portion 122. The user has flipped upper edge 128 downward to expose the loop covering on the inward facing surface of upper portion 122. The user places a second cold pack 112 on this surface by pressing it into position. The user then flips upper edge 128 back upward into position.

Figure 23:
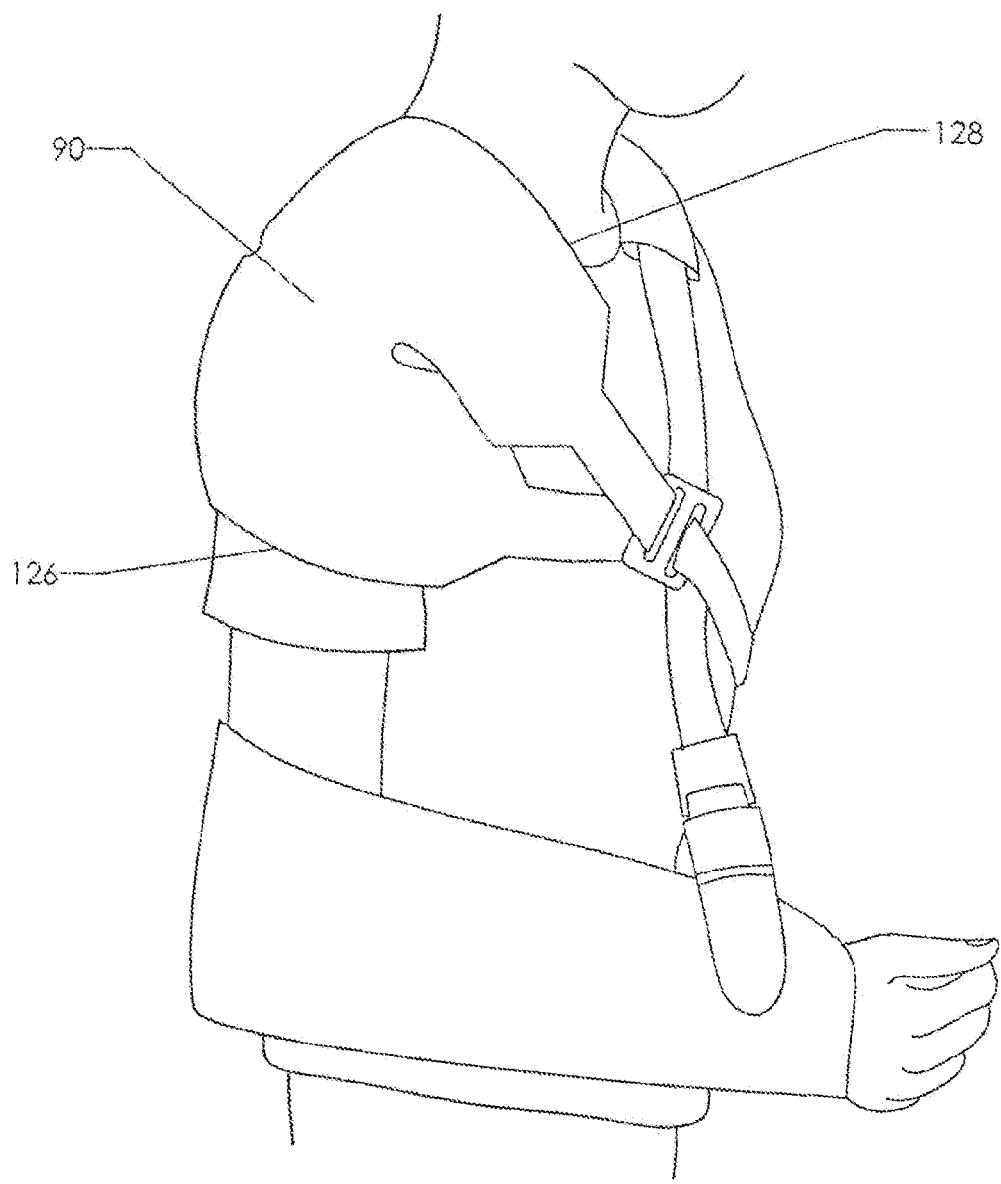
FIG. 23 is a perspective view, showing two cold packs in position on the affected shoulder.

FIG. 23 shows retention panel 90 in position with two of the cold packs installed. The user may optionally adjust the anterior and posterior straps to provide a comfortable fit with the cold packs in place.

Of course, the sequence of steps described can be performed in any desired order. The user may elect to place the upper cold pack first and then place the lower cold pack. The user may only place a single cold pack under the retention panel. The entire inward facing surface of the retention panel is preferably covered in loop material so that the user may place the cold pack(s) in many different positions.

Although the preceding descriptions present considerable detail they should be properly be viewed as illustrating embodiments of the present invention rather than limiting the scope of the invention. Many more embodiments following the same principles will occur to those skilled in the art. For example, snaps or buckles could be substituted for the hook-and-loop attachments described. As a second example, the retention panel could be attached to the patient using attachment points other than the belt. Accordingly, the scope of the invention should be fixed by the following claims rather than by the examples given.

The invention claimed is:

1. A method for placing a cold pack on a shoulder of a patient, said patient having a waist, comprising:
   a. providing a retention panel, said retention panel having an inward facing surface with a portion of said inward facing surface including a loop covering;
   b. providing a belt;
   c. placing said belt around said waist of said user;
   d. providing an anterior strap and a posterior strap;
   e. placing said retention panel on said shoulder of said patient, with said inward facing surface of said retention panel facing said shoulder;
   f. connecting said anterior strap between said retention panel and said belt;
   g. connecting said posterior strap between said retention panel and said belt;
   h. providing a cold pack, said cold pack having a first side and a second side, with said second side including at least one hook panel;
   i. after said retention panel is installed on said shoulder, flipping over at least a portion of said retention panel to expose said loop material on said inward facing surface;
   j. attaching said cold pack to said retention panel by engaging said at least one hook panel on said cold pack with said loop material on said retention panel; and
   k. flipping said at least a portion of said retention panel back over so that said cold pack is placed between said retention panel and said shoulder.

2. A method for placing a cold pack on a shoulder as recited in claim 1, wherein:
   a. said anterior strap is attached to said retention panel by passing said anterior strap through an anterior buckle connected to said retention panel and then attaching said anterior strap to itself; and
   b. said posterior strap is attached to said retention panel by passing said posterior strap through a posterior buckle connected to said retention panel and then attaching said posterior strap to itself.

3. A method for placing a cold pack on a shoulder as recited in claim 1, wherein:
   a. said anterior strap is connected to said belt via a quick release connection; and
   b. said posterior strap is connected to said belt via a quick release connection.

4. A method for placing a cold pack on a shoulder as recited in claim 1, further comprising:
   a. providing a contralateral pad, said contralateral pad having a first connector and a second connector;
   b. attaching said contralateral pad to said belt;
   c. wherein said connection between said anterior strap and said belt is made between said anterior strap and said first connector on said contralateral pad; and
   d. wherein said connection between said posterior strap and said belt is made between said posterior strap and said second connector on said contralateral pad.

5. A method for placing a cold pack on a shoulder as recited in claim 1, wherein:
   a. said retention panel has a first pair of upper and lower extension legs;
   b. said retention panel has a second pair of upper and lower extension legs;
   c. said retention panel has a first connector strap connecting said first pair of upper and lower extension legs, with said first connector strap passing through an anterior buckle; and
   d. said retention panel has a second connector strap connecting said second pair of upper and lower extension legs, with said second connector strap passing through said anterior buckle.

6. A method for placing a cold pack on a shoulder as recited in claim 5, wherein said anterior strap connects to said anterior buckle and said posterior strap connects to said posterior buckle.

7. A method for placing a cold pack on a shoulder as recited in claim 5, wherein said first pair of upper and lower extension legs is separated by a first channel and said second pair of upper and lower extension legs is separated by a second channel.

8. A method for placing a cold pack on a shoulder as recited in claim 1, further comprising:
   a. providing an anterior strap;
   b. providing an anterior buckle connected to said retention panel;
   c. attaching said anterior strap to said retention panel by passing said anterior strap through said anterior buckle and then attaching said anterior strap to itself;
   d. providing a posterior strap;
   e. providing a posterior strap attached to said retention panel;
   f. attaching said posterior strap to said retention panel by passing said posterior strap through said posterior buckle and then attaching said posterior strap to itself.

9. A method for placing a cold pack on a shoulder as recited in claim 8, further comprising:
   a. providing a belt;
   b. attaching said belt to said waist of said patient;
   c. attaching said anterior strap to said belt via a quick release connection; and
   d. attaching said posterior strap to said belt via a quick release connection.

10. A method for placing a cold pack on a shoulder as recited in claim 9, further comprising:
    a. providing a contralateral pad, said contralateral pad having a first connector and a second connector;
    b. attaching said contralateral pad to said belt;
    c. wherein said connection between said anterior strap and said belt is made between said anterior strap and said first connector on said contralateral pad; and
    d. wherein said connection between said posterior strap and said belt is made between said posterior strap and said second connector on said contralateral pad.

11. A method for placing a cold pack on a shoulder of a patient, said patient having a waist, comprising:
    a. providing a retention panel, said retention panel having an inward facing surface with a portion of said inward facing surface including a loop covering;
    b. attaching said retention panel to said shoulder of said patient, with said inward facing surface of said retention panel facing said shoulder;
    c. providing a cold pack, said cold pack having a first side and a second side, with said second side including at least one hook panel;
    d. after said retention panel is installed on said shoulder, flipping over at least a portion of said retention panel to expose said loop material on said inward facing surface;

e. attaching said cold pack to said retention panel by engaging said at least one hook panel on said cold pack with said loop material on said retention panel; and f. flipping said at least a portion of said retention panel back over so that said cold pack is placed between said retention panel and said shoulder.

12. A method for placing a cold pack on a shoulder as recited in claim 11, wherein:
   a. said retention panel has a first pair of upper and lower extension legs;
   b. said retention panel has a second pair of upper and lower extension legs;
   c. said retention panel has a first connector strap connecting said first pair of upper and lower extension legs, with said first connector strap passing through an anterior buckle; and
   d. said retention panel has a second connector strap connecting said second pair of upper and lower extension legs, with said second connector strap passing through said anterior buckle.

13. A method for placing a cold pack on a shoulder as recited in claim 12, wherein said anterior strap connects to said anterior buckle and said posterior strap connects to said posterior buckle.

14. A method for placing a cold pack on a shoulder as recited in claim 12, wherein said first pair of upper and lower extension legs is separated by a first channel and said second pair of upper and lower extension legs is separated by a second channel.

15. A method for placing a cold pack on a shoulder of a patient, said patient having a waist, comprising:
   a. providing a retention panel, said retention panel having an inward facing surface with a portion of said inward facing surface including a loop covering;
   b. providing an anterior attachment point and a posterior attachment point for said retention panel;
   c. placing said retention panel on said shoulder of said patient, with said inward facing surface of said retention panel facing said shoulder;
   d. connecting said anterior attachment point and said posterior attachment point of said retention panel to said patient;
   e. providing a cold pack, said cold pack having a first side and a second side, with said second side including at least one hook panel;
   f. after said retention panel is installed on said shoulder, flipping over at least a portion of said retention panel to expose said loop material on said inward facing surface;
   g. attaching said cold pack to said retention panel by engaging said at least one hook panel on said cold pack with said loop material on said retention panel; and
   h. flipping said at least a portion of said retention panel back over so that said cold pack is placed between said retention panel and said shoulder.

16. A method for placing a cold pack on a shoulder as recited in claim 15, wherein:
   a. said anterior attachment point on said patient is connected to said patient via an anterior strap; and
   b. said posterior attachment point on said patient is connected to said patient via a posterior strap.

17. A method for placing a cold pack on a shoulder as recited in claim 16, further comprising:
   a. providing a belt;
   b. attaching said belt to said waist of said patient;
   c. attaching said anterior strap to said belt; and
   d. attaching said posterior strap to said belt.

18. A method for placing a cold pack on a shoulder as recited in claim 17, further comprising:
   a. providing a contralateral pad, said contralateral pad having a first connector and a second connector;
   b. attaching said contralateral pad to said belt;
   c. wherein said connection between said anterior strap and said belt is made between said anterior strap and said first connector on said contralateral pad; and
   d. wherein said connection between said posterior strap and said belt is made between said posterior strap and said second connector on said contralateral pad.

19. A method for placing a cold pack on a shoulder as recited in claim 15, wherein:
   a. said retention panel has a first pair of upper and lower extension legs;
   b. said retention panel has a second pair of upper and lower extension legs;
   c. said retention panel has a first connector strap connecting said first pair of upper and lower extension legs, with said first connector strap passing through an anterior buckle; and
   d. said retention panel has a second connector strap connecting said second pair of upper and lower extension legs, with said second connector strap passing through said anterior buckle.

20. A method for placing a cold pack on a shoulder as recited in claim 19, wherein said first pair of upper and lower extension legs is separated by a first channel and said second pair of upper and lower extension legs is separated by a second channel.

* * * * *